(12) United States Patent
Sanders et al.

(10) Patent No.: US 7,929,902 B1
(45) Date of Patent: Apr. 19, 2011

(54) VIRTUAL WIRELESS MULTITRACK RECORDING SYSTEM

(75) Inventors: Glenn Norman Sanders, Franklin Lakes, NJ (US); Howard Glenn Stark, Sparta, NJ (US)

(73) Assignee: Zaxcom, Inc., Pompton Plains, NJ (US)

(*) Notice: Subject to any disclaimer, the term of this patent is extended or adjusted under 35 U.S.C. 154(b) by 1135 days.

(21) Appl. No.: 11/404,735

(22) Filed: Apr. 14, 2006

Related U.S. Application Data

(63) Continuation-in-part of application No. 11/181,062, filed on Jul. 14, 2005, now Pat. No. 7,711,443.

(51) Int. Cl.
H04H 40/00 (2008.01)
H04B 7/00 (2006.01)
H04K 11/00 (2006.01)

(52) U.S. Cl. ............... 455/3.06; 455/66.1; 455/344

(58) Field of Classification Search ............ 455/3.01, 455/3.06, 66.1, 344, 412.1
See application file for complete search history.

(56) References Cited

U.S. PATENT DOCUMENTS

| | | | | |
|---|---|---|---|---|
| 5,668,884 | A * | 9/1997 | Clair et al. | 381/82 |
| 6,678,501 | B1 * | 1/2004 | Valeski | 455/3.04 |
| 6,970,568 | B1 * | 11/2005 | Freeman et al. | 381/58 |
| 6,978,116 | B2 * | 12/2005 | Burr et al. | 455/3.02 |
| 7,120,463 | B2 * | 10/2006 | Mathews | 455/557 |
| 7,162,227 | B2 * | 1/2007 | Howard | 455/416 |
| 7,277,551 | B2 * | 10/2007 | Miura et al. | 381/98 |
| 7,295,809 | B2 * | 11/2007 | Moore | 455/41.2 |
| 7,409,064 | B2 * | 8/2008 | Watanuki | 381/74 |
| 7,440,750 | B2 * | 10/2008 | Howard | 455/416 |
| 7,451,177 | B1 * | 11/2008 | Johnson et al. | 709/203 |
| 7,711,443 | B1 * | 5/2010 | Sanders et al. | 700/94 |
| 7,751,795 | B2 * | 7/2010 | McCarty et al. | 455/402 |
| 2001/0034214 | A1 * | 10/2001 | Koike | 455/95 |
| 2002/0193066 | A1 * | 12/2002 | Connelly | 455/2.01 |
| 2005/0266801 | A1 * | 12/2005 | Mathews | 455/66.1 |
| 2006/0292980 | A1 * | 12/2006 | Marcos Alba | 455/3.06 |
| 2007/0087686 | A1 * | 4/2007 | Holm et al. | 455/3.06 |

* cited by examiner

*Primary Examiner* — Tilahun Gesesse
(74) *Attorney, Agent, or Firm* — Chipperson Law Group

(57) ABSTRACT

Disclosed are systems and methods for wirelessly recording multi-track audio files without the data corruption or loss of data that typically occurs with wireless data transmission. In some aspects of the present invention, each performer is equipped with a local audio device capable of locally recording the respective performer's audio while also transmitting it to a master recorder. The locally recorded audio may then be used to repair or replace any audio lost or corrupted during transmission to the master recorder. Such repair or replacement may be performed electronically or via playback of the locally recorded audio. In other aspects of the present invention, a master recorder is not required since all locally recorded audio may be combined or otherwise processed post-recording. Locally recorded audio may include identifiers to aid in post-recording identification of such audio. A multi-memory unit is also provided to facilitate manipulation and processing of audio files.

20 Claims, 13 Drawing Sheets

400

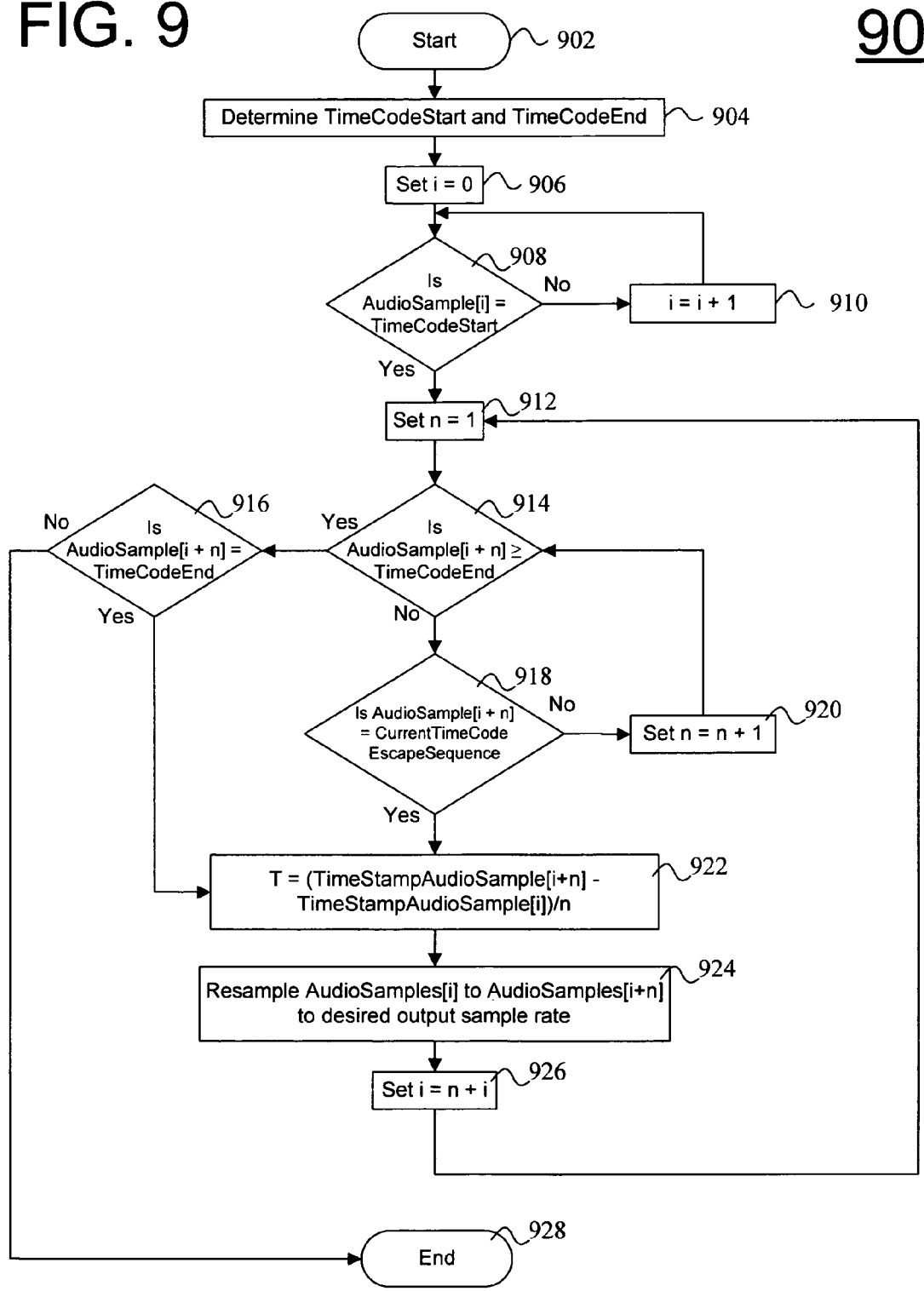

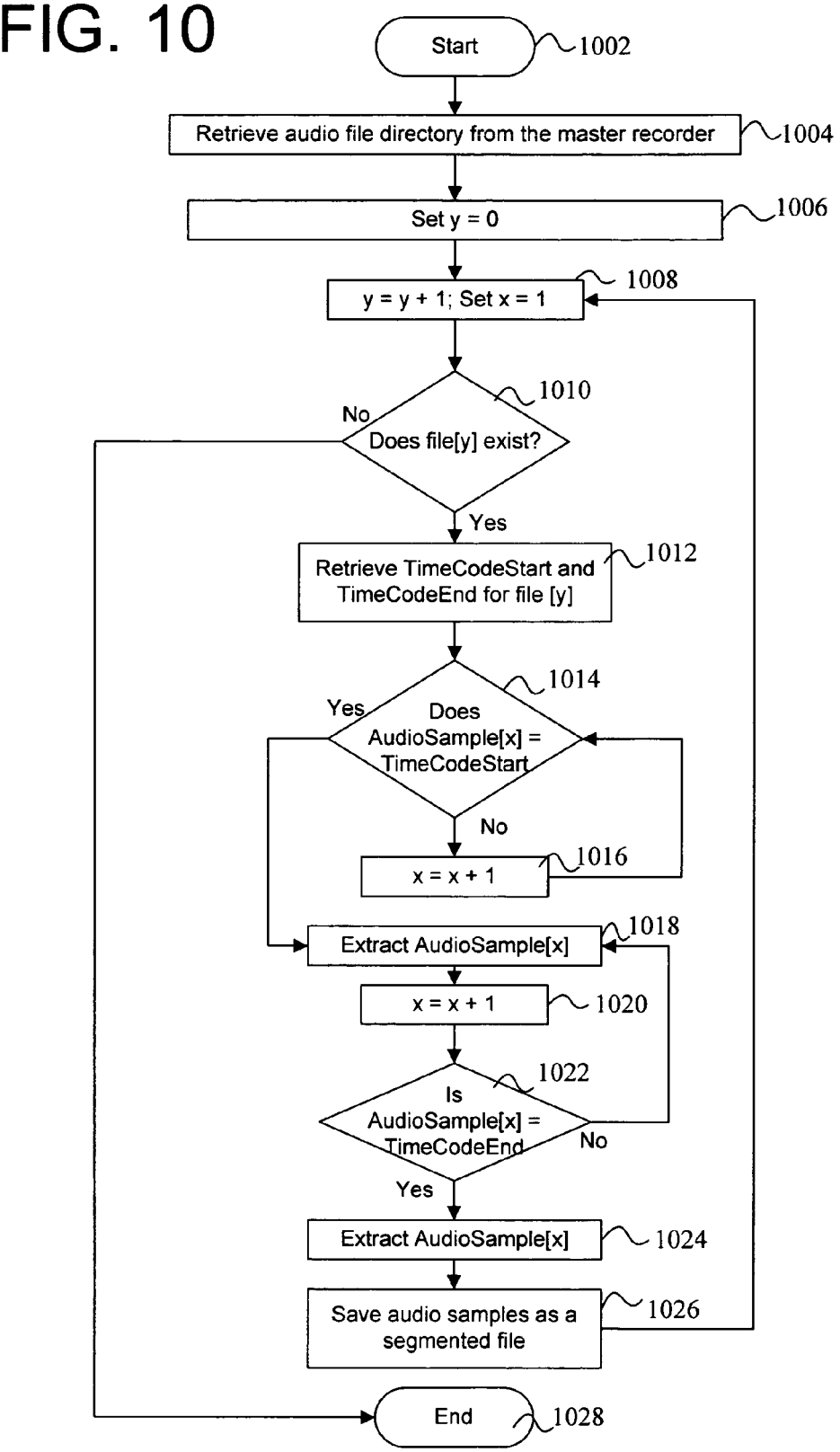

VIRTUAL WIRELESS MULTITRACK RECORDING SYSTEM

CROSS-REFERENCE TO RELATED APPLICATIONS

This application claims the benefit of and is a continuation-in-part of the U.S. patent application entitled "Virtual Wireless Multitrack Recording System", having Ser. No. 11/181,062, filed Jul. 14, 2005, now U.S. Pat. No. 7,711,443, which is incorporated by reference in its entirety as if fully set forth herein.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyrights whatsoever.

BACKGROUND OF THE INVENTION

Embodiments of the present invention generally relate to systems and methods for recording and processing audio received from one or more wireless devices. More specifically, the present invention relates to systems and methods for recording and processing audio having one or more tracks received from one or more wireless devices operating in either an asynchronous or synchronous mode.

Many systems and methods have been created to record performance audio. Some such systems include a multi-track audio recorder wired to one or more microphones. Typically, one or more performers performing on a sound stage are recorded by one or more microphones that are directly wired to the multi-track recorder. The multi-track recorder combines the single track of audio received from each microphone to create one multi-track audio file. In many such systems, the received audio and/or the multi-track audio is timestamped with a time reference signal such as a Society of Motion Picture and Television Engineers ("SMPTE") timecode signal containing information regarding the hour, minute, second, frame, type of timecode (i.e., nondrop or drop frame), and user-definable information. Such information allows audio to be more easily matched and/or combined with simultaneously recorded video.

Other such systems include a multi-track audio recorder and an associated audio receiver that receive audio wirelessly from one or more wireless transmitters. Such wireless transmitters may take the form of body packs that are worn by each performer. Typically, the audio receiver receives each performer's audio from the performer's respective body pack via an analog or digital wireless transmission and transmits it to the audio recorder. The audio recorder then combines the wireless transmissions received from all body packs to create one multi-track audio file.

Due to the occurrence of wireless transmission errors such as dropouts, some existing wireless systems include audio receivers having two or more redundant receiver circuits. The incorporation of additional, redundant receiver circuits provides a better opportunity to avoid missed audio transmissions. For example, the use of two receiver circuits may allow a second receiver to receive audio that may have not been received by a first receiver circuit and vice versa. However, although such redundancy accounts may correct wireless transmission errors, such redundancy does not prevent loss of data due to interference (i.e., a distortion of the received audio signal due to receipt of multiple wireless signals). Upon the occurrence of interfering signals, audio created during a performance (e.g., a live performance) may simply be lost due to the inability of the receiver to receive a clean audio signal.

BRIEF SUMMARY OF THE INVENTION

Briefly stated, in one aspect of the present invention, a system for recording locally generated audio is provided. This system includes at least one master timecode generator for generating a plurality of master timecodes, and at least one local audio device wearable by a creator of said locally generated audio including at least one local audio device receiver for receiving at least one of the group consisting of digital commands, master timecodes, and non-local audio data; at least one audio input port for receiving locally generated audio from an audio input device; at least one memory; and at least one control unit electrically coupled to the local audio device receiver, the audio input device, and the memory for creating local audio data from said locally generated audio and storing the local audio data in the memory; wherein the local audio data includes stamped local audio data and unstamped local audio data; wherein the stamped local audio data includes at least one first timestamp reference at least a portion of the local audio data to at least one of the master timecodes; and wherein the unstamped local audio data does not include a reference to the master timecodes.

In another aspect of the present invention, disclosed is a system for recording locally generated audio. This system includes at least one master timecode generator for generating a plurality of master timecodes, and at least one local audio device wearable by a creator of said locally generated audio including at least one local audio device receiver for receiving at least one of the group consisting of digital commands and the master timecodes; at least one audio input port for receiving locally generated audio from an audio input device; at least one memory; at least one local timecode generator for generating a plurality of local timecodes; and at least one control unit electrically coupled to the local audio device receiver, the audio input device, the memory, and the local timecode generator for creating stamped local audio data and storing the stamped local audio data in the memory; wherein the stamped local audio data includes at least one local timestamp to reference at least a portion of the stamped local audio data to at least one of the local timecodes; and wherein the stamped local audio data includes at least one identifier selected from the group consisting of track identifiers, local audio device identifiers, performer identifiers, and combinations thereof.

In another aspect of the present invention, a method of wirelessly recording local audio is provided. This method includes locally receiving the local audio generated by at least one performer during an audio event; wirelessly transmitting the local audio to at least one of the group consisting of a recorder, a receiver, and combinations thereof; locally recording the local audio as local audio data in at least one memory of at least one local audio device; and remotely recording the transmitted local audio via at least one of the group consisting of a recorder, a receiver, and combinations thereof as remote audio data; wherein at least a portion of the local audio data is retrieved during or subsequent to the audio event and is combined with the remote audio data; and wherein the local audio data includes at least one identifier selected from the group consisting of track identifiers, local audio device identifiers, performer identifiers and combinations thereof.

In another aspect of the present invention, a method for recording local audio is provided. The method includes locally receiving local audio generated by at least two performers during an audio event; locally recording local audio as local audio data in at least one memory of at least one local audio device; and locally receiving or generating a plurality of master timecodes; wherein the local audio data for each of the performers is retrieved from the local audio devices subsequent to the audio event and is combined to create a single multi-track audio file; wherein the local audio data includes at least one identifier selected from the group consisting of track identifiers, local audio device identifiers, performer identifiers, and combinations thereof; wherein said local audio data includes stamped local audio data and unstamped local audio data; wherein said stamped local audio data includes at least one first timestamp to reference at least a portion of said local audio data to at least one of said master timecodes; wherein said unstamped local audio data does not include a reference to said master timecodes; and wherein said master timecode includes at least one of the group consisting of time data, frame data, timecode type, recorder transport status, name of scene, name of take, track identifier, and combinations thereof.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments that are presently preferred. It should be understood, however, that the invention is not limited to the precise arrangements and instrumentalities shown. In the drawings:

FIG. 9 depicts a process for interpolating timestamps for unstamped audio samples based upon the timestamps of stamped audio samples, and resampling the audio samples to include the interpolated timestamps in accordance with one embodiment of the present invention.

FIG. 10 depicts a process for segmenting a single large audio file into multiple smaller files that correlate to a master directory of files in accordance with one embodiment of the present invention.

DETAILED DESCRIPTION OF THE INVENTION

Figure 1:
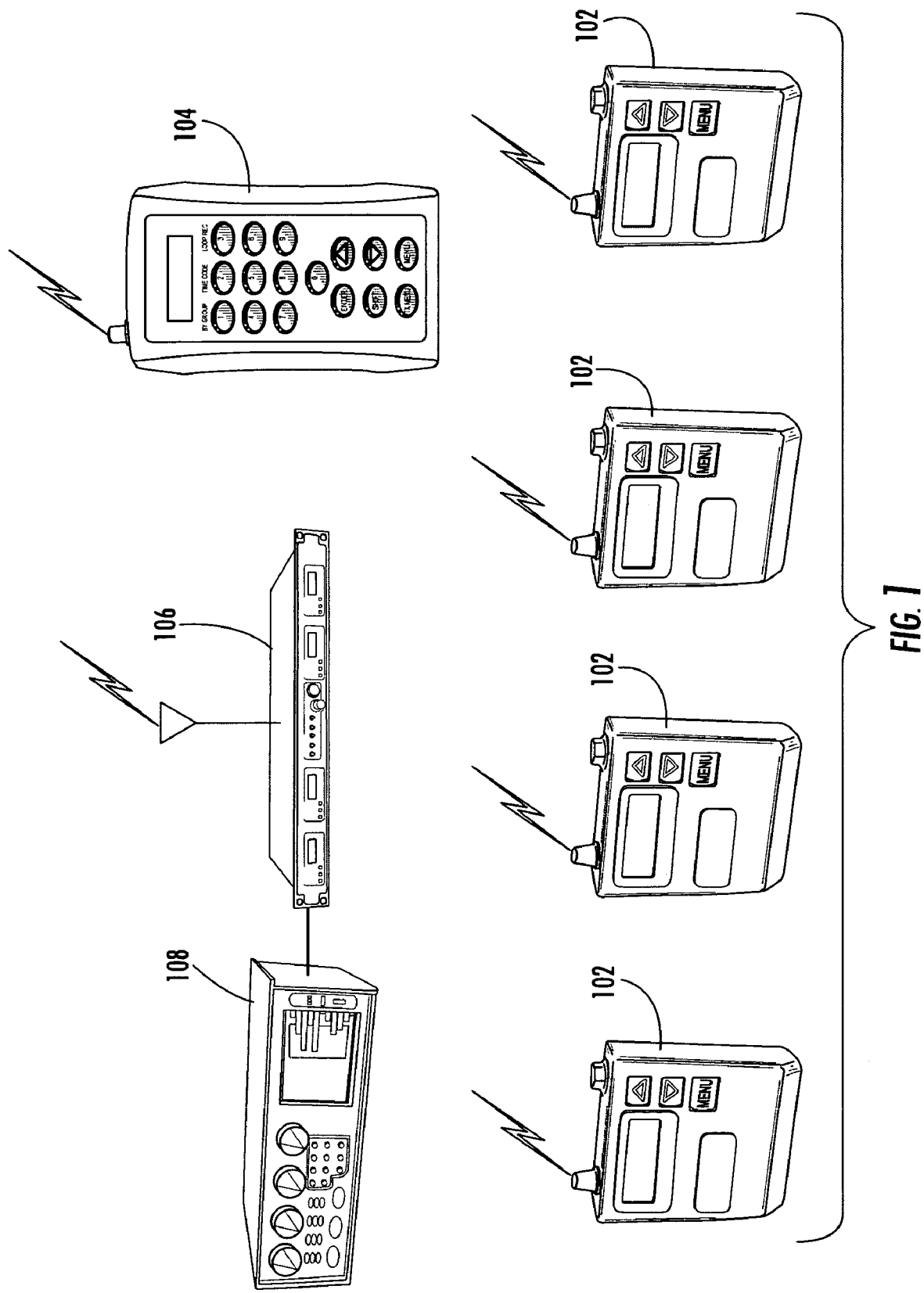
FIG. 1 depicts the components of a recording system in accordance with one embodiment of the present invention including, inter alia, local audio devices, a remote control unit, a receiver, and a recorder.

Referring first to FIG. 1, depicted is recording system 100 in accordance with one embodiment of the present invention. Recording system 100 wirelessly records audio events, such as performances, movie takes, etc. having one or more performers. In one aspect of the present invention, all of the components of recording system 100 are synchronized to allow each component to accurately stamp its recorded audio with the time at which it occurred such that the timestamps (i.e., information stored with an audio sample or audio file conveying the time at which the audio sample or first audio sample of the file occurred) created by each individual component of recording system 100 are highly accurate as compared to the timestamps created by all other components of recording system 100. This accuracy allows multiple individually recorded audio tracks to be combined into one or more multi-track audio files electronically post-recording. Furthermore, this accuracy allows recording system 100 to automatically correct for any audio data lost during an original recording due to wireless transmission problems such as dropout, interference, etc. This automatic correction may be performed either electronically or via synchronized playback of the individually recorded audio tracks. In another aspect of the present invention, the audio recorded by recording system 100 may be recorded asynchronously. In this scenario, the audio is synchronized and/or mixed post-recording to automatically correct for any audio data lost due to wireless transmission problems such as dropout, interference, etc.

In the embodiment of the present invention depicted in FIG. 1, recording system 100 includes local audio devices 102, remote control unit ("RCU") 104, receiver 106, and recorder 108. In one embodiment, RCU 104 includes an RF transmitter capable of transmitting one or more of a time reference signal, digital commands, and audio to one or more other components of recording system 100. Additionally, RCU 104 may be equipped with the capability of remotely controlling local audio devices 102, receiver 106, and recorder 108 to perform tasks including, but not limited to, initiating audio playback of all local audio devices 102 starting at the same time reference, as well as recording thereof by receiver 106 and recorder 108.

Both live and replayed audio transmitted by local audio devices 102 may be received at receiver 106 and recorded by audio recorder 108. Receiver 106 and recorder 108 may be virtually any commercially available receiver and recorder. Receiver 106 receives the wireless RF signals (e.g., modulated RF carrier signals) generated by all active local audio devices 102 and converts the signals to a format capable of being recorded by a commercially available recording device including, but not limited to, Zaxcom, Inc.'s DEVA® multi-track recorder. In some embodiments, such commercially available recording devices record audio with a locally generated SMPTE-compatible timecode signal.

The ability to synchronize the local timestamps at each local audio device 102 and recorder 108 using the methods of the present invention as discussed in greater detail below allows any audio that is not recorded by recorder 108 during an event due to transmission errors to be recovered by replaying the missed audio and recording the replayed audio in the correct time sequence with respect to the other audio samples. In other words, since the audio samples are stored locally in each local audio device 102 with timestamps that are synchronized with the timestamps of recorder 108, whenever audio is not recorded at recorder 108, it may simply be replayed at local audio devices 102 starting at the timecode of the missed audio. Since the local audio device and recorder timestamps are synchronized, the replayed audio may be inserted in the proper time sequence with respect to the other recorded audio samples based upon the synchronized timestamp data. Synchronization is essential to ensure that each performer's audio is synchronized with all other performers' audio and to ensure that the newly recorded replayed audio is in the correct sequence with respect to the previously recorded live audio. Such synchronization must maintain a high accuracy for each performer's timestamps with respect to all other performers' timestamps to prevent the occurrence of phasing artifacts when the multiple audio recordings are combined to create one single recording.

In some embodiments of the present invention, receiver 106 automatically senses an error in transmission caused by, for example, a communication loss, interference, etc. In some embodiments of the present invention, the error in transmission is sensed by comparing a calculated checksum to the transmitted checksum to determine if data was lost during transmission. An error is determined if the calculated and transmitted checksums do not match. Upon sensing a transmission error, receiver 106 may transmit a request to RCU 104 requesting playback of the audio recorded locally on local audio devices 102 beginning at a timecode prior to the occurrence of the transmission error. In response, RCU 104 transmits a digital command to all local audio devices 102 to playback the audio stored in the respective memory 332 (FIG. 3) that occurred subsequent to the timecode requested by receiver 106 in the manner described below with respect to FIG. 6.

Alternatively, playback may be requested manually by a user of a recording system such as recording system 100. In this scenario, upon hearing that a transmission error (i.e., a loss of audio data) has occurred, the user manually prompts RCU 104 to transmit a digital command to all local audio devices 102 to playback the audio stored in memory 332 (FIG. 3) that occurred subsequent to a time reference entered at RCU 104 by the user. Such prompting may occur after the audio event ends or immediately upon hearing the transmission error. If the latter option is chosen, prompting playback of a specific segment of the audio event may index the local audio devices to store the requested data in a protected memory location until the end of the audio event to avoid disrupting the recording. In this scenario, all requested audio shall be replayed after the performance ends. In embodiments of the present invention in which data is recorded in a loop (i.e., when memory is full, new data overwrites previously recorded data), writing the data to a protected memory location removes it from the loop and protects it from being overwritten.

Figure 2A:
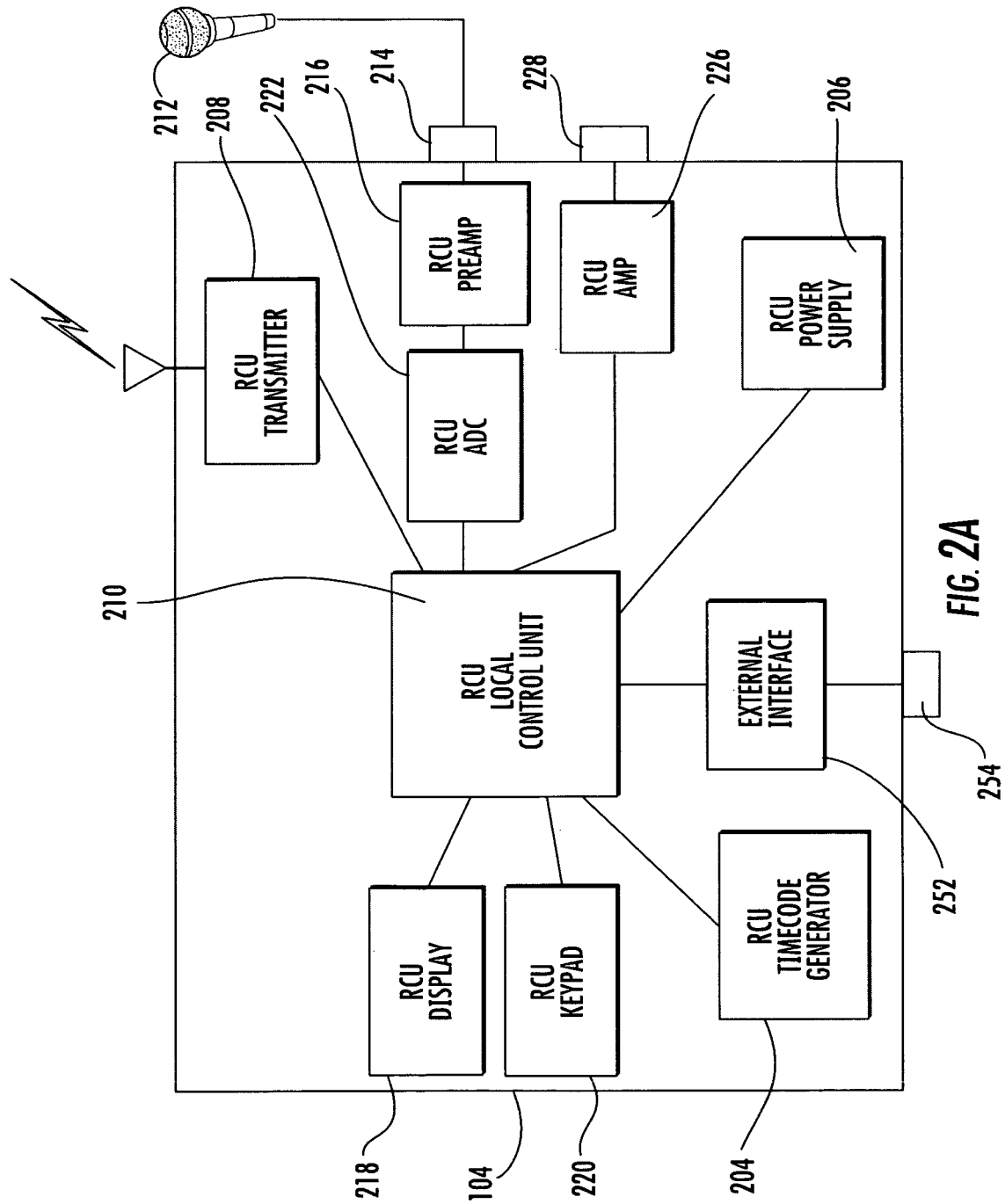
FIG. 2A depicts a block diagram of the internal components of a remote control unit in accordance with one embodiment of the present invention.

FIG. 2A depicts a block diagram of one embodiment of RCU 104 in accordance with the present invention. In this embodiment, RCU 104 includes, inter alia, RCU timecode generator 204, RCU power supply 206, RCU transmitter 208, RCU local control unit 210, RCU audio input device 212, RCU audio input device port 214, RCU preamp 216, RCU display 218, RCU keypad 220, RCU ADC 222, RCU amp 226, timecode input port 228, external interface 252, and external interface port 254.

RCU transmitter 208 allows RCU 104 to transmit a master time reference signal, digital commands, audio, and the like to other devices such as local audio devices 102, receiver 106, and recorder 108. In one aspect of the present invention, the time reference signal is a SMPTE timecode signal containing information regarding the hour, minute, second, frame, type of timecode (i.e., nondrop or drop frame), and user-definable information (e.g., the transport status of recorder 108, the name of a scene, the name of a take, a local audio device identifier that identifies the local audio device that recorded the respective audio, a track identifier that identifies the track of audio which may include the actor or actress recording the respective audio, etc.). This master time reference signal provides a time reference for all local audio devices 102, which may use this information for a variety of purposes such as jam synchronizing their respective local timecode generators 304 (FIG. 3A), adjusting the speed of the local timecode generators 304 (FIG. 3A), timestamping locally recorded audio, etc. The master time reference signal may be generated on board remote control unit 104 via a mechanism such as RCU timecode generator 204. Or, alternatively, the master time reference signal may be generated by an independent timecode generator that transmits timecodes to remote control unit 104 wirelessly or via a cable or the like connected from the independent timecode generator to timecode input port 228. In the latter scenario, the timecodes received via timecode input port 228 are buffered and/or amplified by RCU amp 226 prior to transmission to RCU local control unit 210.

When recording system 100 is operating in a synchronous mode, transmission of the master time reference signal ensures that all of the components of recording system 100 store all locally recorded audio with timestamps that are highly accurate as compared to the timestamps of all other local audio devices 102 and/or all other components of recording system 100. The timestamps are then used during playback and recording to ensure that the replayed audio from all local audio devices 102 is synchronized with previously recorded audio and with the audio replayed by all other local audio devices 102. In contrast, when recording system 100 is operating in an asynchronous mode, transmission of the master time reference signal allows the files containing recorded audio to be timestamped with the master time reference information to allow the recorded audio to be accurately synchronized post-recording.

RCU transmitter 208 also allows audio generated locally at RCU 104 to be transmitted to the other components of recording system 100. Such audio may be received from an audio input device such as RCU audio input device 212 via audio input device port 214. RCU audio input device 212 may be any type of commercially available audio input device such as a microphone and audio input device port 214 may be any commercially available audio input device port that is compatible with RCU audio input device 212 and the internal components of RCU 104. The received audio as well as any digital signals (e.g., microphone input level, line input level, etc.) are then buffered and/or amplified by RCU preamp 216 and are converted from analog to digital by RCU ADC 222 such that the audio may be read in digital form by RCU local control unit 210. This audio may then be processed and sent via RCU transmitter 208 in either analog or digital form. If the audio is to be sent in analog form, RCU local control unit 210 may be equipped with an on-board DAC or an independent DAC may be incorporated in RCU 104 without departing from the scope of the present invention. Or, alternatively, analog audio received from RCU audio input device 212 may be passed directly to RCU transmitter 208 for transmission in analog form to the other components of the recording system. In such embodiments, RCU transmitter 208 may be equipped with a frequency modulation ("FM") modulator or the like.

Furthermore, in such embodiments, although the analog audio is passed through to RCU transmitter 208, the audio signal may be additionally converted to digital form for local recording of the received audio. In yet another alternate embodiment, audio may be transmitted and recorded in analog form thereby eliminating RCU ADC 222.

In the aforementioned embodiments in which the audio signal for a particular track of audio is converted to digital form for local recording of the received audio, identifiers such as a local audio device identifier that identifies the local audio device that recorded the respective audio, a track identifier that identifies the track of audio which may include the actor or actress recording the respective audio, etc. may be recorded with the recorded audio to allow the audio tracks to be easily and quickly identified post-recording and/or post-production. In some embodiments of the present invention, such identification information is stored in the local, nonvolatile memory of the local audio device as a text file, however, the present invention is not so limited. In another aspect of the present invention, such identification information is encoded in the audio file such that it may be decoded post-recording and/or post-production using methods known in the art. Additionally, such identification information may be integral to a timecode or completely distinct therefrom. Furthermore, such identification information may be programmed for each local audio device remotely via a remote control unit such as RCU 104.

In some embodiments of the present invention, RCU local control unit 210 may be a digital signal processor such as Texas Instruments part number TMS320C5509A. However, the present invention is not so limited. Any combination of hardware and software may be substituted for any component described herein without departing from the scope of the present invention.

Figure 2B:
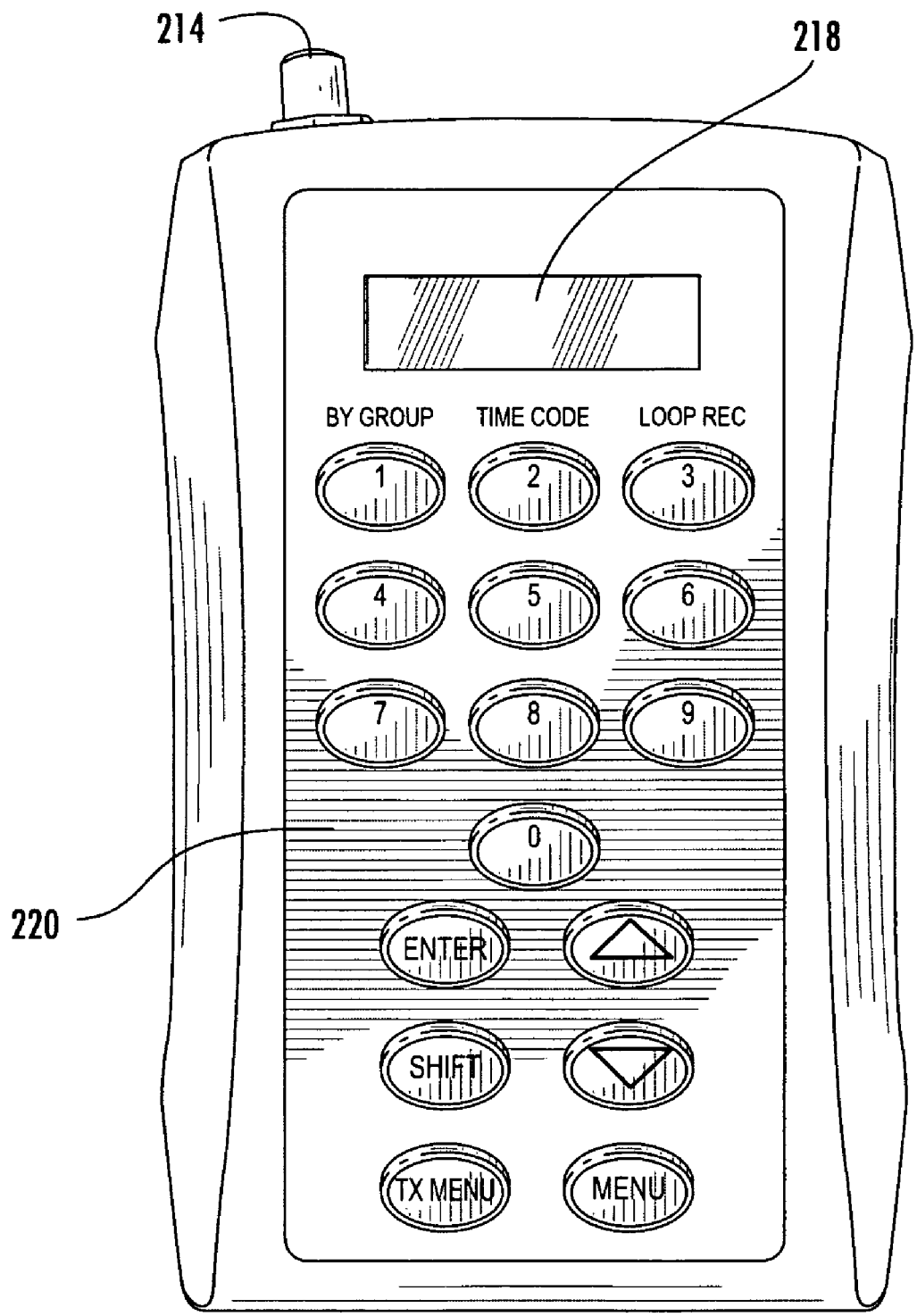
FIG. 2B depicts an external view of a remote control unit in accordance with one embodiment of the present invention.

RCUs 104 may be handheld units such as RCU 104 depicted in FIG. 2B. In such an embodiment, display 218 may be a small liquid crystal display ("LCD") or the like and keypad 220 may include a plurality of buttons that allow a user to perform local RCU functions including, but not limited to, those that relate to RCU transmitter frequency, group identification ("ID") code, unit ID code, and timecode generator mode. For example, the RCU transmitter frequency may be adjustable in predetermined frequency steps. In most cases, this frequency will be set to match the receiving frequency of other devices in the recording system (e.g., local audio devices). Or, when multiple local audio devices are incorporated into a group with an RCU, the RCU as well as other components of the recording system (e.g., local audio devices) may be assigned a group ID to ensure that the RCU is controlling the correct group of local audio devices. Similarly, the unit ID identifies the specific one of multiple local audio devices that a user wishes to control. Setting the unit ID ensures that the control signals transmitted by the RCU are received by the correct local audio device. Also, timecode generator mode allows the RCU to either generate its own timecodes or to receive timecodes from an external timecode generator.

In addition to allowing a user to modify local RCU settings, RCU keypad 220 and display 218 also allow the RCU to remotely control individual local audio devices. The user may perform a variety of functions for the local audio device including, but not limited to, transmitter and receiver frequencies, transmitter enable, microphone gain, high pass filter, record mode select, time code entry, playback control, audio bank storage, and status request.

For example, local audio device transmitter and receiver frequencies may be adjustable in predetermined frequency steps. Alternatively, the local audio device transmitter may be remotely enabled and disabled. Microphone gain may be adjusted, which in turn adjusts the current setting of a preamp such as local preamp 316. Adjustment of the high pass filter may be incorporated to enable and disable, or otherwise adjust, the high pass audio filter of the audio input device such as audio input device 312.

In addition, record mode select allows recording modes such as endless loop record mode or timed record mode to be remotely adjusted. Timecodes may also be set remotely for each local audio device. Playback control allows one or more local audio devices to be commanded remotely to playback audio starting at a specific timecode. Completion of playback may be automatically or manually determined. Functions such as audio bank storage allow a remote user to manually store chunks of audio data in safe locations of the local audio device memory (i.e., in locations in which the audio data will not be overwritten). Finally, status of the local audio device may be requested. The status may be provided via display 218 or via spoken language generated by local audio device 102 and transmitted to a receiver or receiver/recorder combination for recording with the recorded audio.

The RCU may also allow a user to program data at each local audio device such as track identifiers, local audio device identifiers, and the like. In such scenarios, such identifiers are recorded with the respective audio to allow the track, local audio device, etc. of the recorded audio to be identified post-recording. That is, each segment of recorded audio may be associated with a specific take, track, or the like, as well as a specific local audio device. Such association allows each portion of recorded audio (e.g., a track of audio) to be quickly and easily identified post-production and/or post-recording without confusion.

Although many specific features and functions for the RCU have been delineated herein, other features and functions may be added or eliminated without departing from the scope of the present invention.

Additionally, handheld embodiments may include any one of a variety of commercially available batteries to function with the power supply 206 without departing from the scope of the present invention. Power supply 206 may be virtually any power component or combination thereof that is compatible with the other components of RCU 104 including, but not limited to, a Texas Instruments TPS62000DGS Power Module alone or in combination with a Linear Technology LTC3402 Synchronous Boost Converter.

However, non-handheld embodiments of RCU 104 are also envisioned such as tabletop models, personal computer ("PC") models, etc. Also, RCU 104 may be optionally equipped with external interface 252 (FIG. 2A) to facilitate connection of RCU 104 to a PC, laptop PC, dumb terminal, or the like via external interface port 254. Such an interface allows a user to control the components of recording system 100 via a graphical user interface or other software that may operate on a larger user interface. Such an interface may provide more features and functions than that available on a portable, handheld device such as programming and execution of complex playback scenarios, automatic initiation of complex playback scenarios based upon detected audio transmission errors, etc.

Figure 3A:
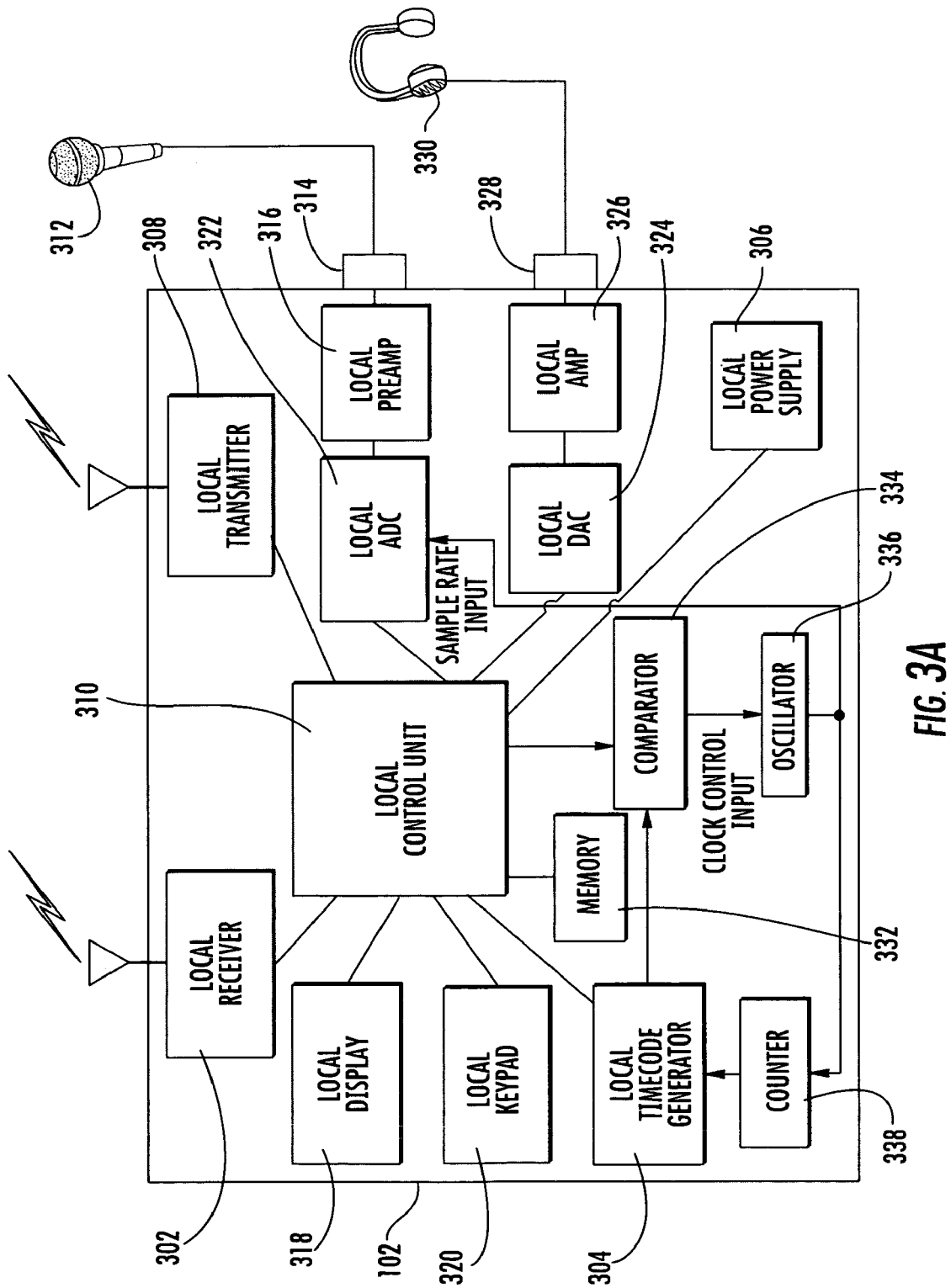
FIG. 3A depicts a block diagram of the internal components of a local audio device in accordance with one embodiment of the present invention.

Turning next to FIG. 3A, depicted is a block diagram of one embodiment of local audio device 102 in accordance with the present invention. In one aspect of the present invention, local audio devices 102 are digital, wireless audio transceivers. Such audio devices may be manufactured in the form of body-packs, such as those typically worn by news announcers, performers, and the like. In the depicted embodiment, local audio device 102 includes, inter alia, local receiver 302, local timecode generator 304, local power supply 306, local transmitter 308, local control unit 310, local audio input device 312, local audio input device port 314, local preamp 316, local display 318, local keypad 320, local ADC 322, local DAC 324, local amp 326, local audio output device port 328, local audio output device 330, memory 332, comparator 334, oscillator 336, and counter 338.

Local transmitter 308 also allows audio generated locally at local audio device 102 to be transmitted to the other components of recording system 100. Such audio may be received from an audio input device such as local audio input device 312 via local audio input device port 314. Local audio input device 312 may be any type of commercially available audio input device such as a microphone and local audio input device port 314 may be any commercially available audio input device port that is compatible with local audio input device 312 and the internal components of local audio device 102. The received audio as well as any digital signals (e.g., microphone input level, line input level, etc.) are then buffered and/or amplified by local preamp 316 and are converted from analogic) digital by local ADC 322 such that the audio may be read in digital form by local control unit 310. This audio may then be processed and sent via local transmitter 308 in either analog or digital form. If the audio is to be sent in analog form, local control unit 310 may be equipped with an on-board DAC or an independent DAC may be incorporated in local audio device 102 without departing from the scope of the present invention. Or, alternatively, analog audio received from local audio input device 312 may be passed directly to local transmitter 308 for transmission in analog form to the other components of the recording system. In such embodiments, local transmitter 308 may be equipped with a frequency modulation ("FM") modulator or the like. Furthermore, in such embodiments, although the analog audio is passed through to local transmitter 308, the audio signal may be additionally converted to digital form for local recording of the received audio. In yet another alternate embodiment, audio may be transmitted and recorded in analog form thereby eliminating local ADC 322.

In some embodiments of the present invention, local control unit 310 may be a digital signal processor such as Texas Instruments part number TMS320C5509A. However, the present invention is not so limited. Any combination of hardware and software may be substituted for any component described herein without departing from the scope of the present invention.

Similarly, local receiver 302 allows audio received from other components of recording system 100 to be played locally at local audio device 102. Such audio may be received in either analog or digital form at local receiver 302. However, if the audio is to be received in analog form, local control unit 310 may be equipped with an on-board ADC or an independent ADC may be incorporated in local audio device 102 without departing from the scope of the present invention to allow local control unit 310 to receive the audio in digital form. Thereafter, the audio may be processed or relayed directly to local DAC 324, which converts the audio data back to analog form. The analog audio may then be amplified by local amp 326 prior to transmission through local audio output device port 328 to local audio output device 330. Local audio output device 330 may be any type of commercially available audio output device such as headphones, speakers, and the like, and local audio output device port 328 may be any commercially available audio output device port that is compatible with local audio output device 330 and the internal components of local audio device 102. Local receiver 302 may be virtually any receiver compatible with the other components of local audio device 102 including, but not limited to, a Micrel Semiconductor MICRF505 RadioWire® transceiver.

Memory 332 of local audio device 102 locally stores audio processed by local control unit 310 in one or more audio files. In one aspect of the present invention, local control unit 310 receives recordable audio from local audio input device 312, which may be worn by the performer and connects to local audio device 102 at local audio input device port 314. However, in alternate embodiments, local control unit 310 may also receive audio from other components of recording system 100 via local receiver 302. The locally stored audio files may include identification data such as local audio device identifiers, track identifiers, performer identifiers, and the like as discussed in greater detail above. Furthermore, the locally stored audio files include timestamps (e.g., timestamps may be stored in the header of the audio file) that indicate when, during the audio event, each segment of audio occurred. The timestamps may be generated based upon timecodes created by local timecode generator 304 or based upon master timecodes. Such master timecodes may be received using a plurality of methods or components including, but not limited to, wirelessly from a master timecode source through local receiver 302, from a timecode source connected to local audio input device port 314, and from local audio input device 312 wherein the master timecodes are received from an ultrasonic signal. Local timecode generator 304 may be synchronized with the master timecode generator during recording of the audio event as described in further detail below with respect to FIG. 5. Or, alternatively, the timestamps may be synchronized post-recording as described in further detail below with respect to FIGS. 9 and 10. Simultaneous with the local recording of audio received from local audio input device 312, this audio may also be transmitted through local transmitter 308 to receiver 106 and/or recorder 108 to allow recording of the audio event. In this scenario, receiver 106 and/or recorder 108 may simultaneously record a multi-track recording of all of the single tracks of audio received from local audio devices 102, which are worn by the performers of the audio event.

Memory 332 may be virtually any type of commercially available removable or non-removable memory including, but not limited to, flash memory cards, compact flash memory cards, Universal Serial Bus ("USB") thumbdisks, and the like. Use of removable memories 332 facilitates removal and insertion of these memories into a PC or the like for electronic combination or mixing of the recorded audio data. Such electronic mixing may be performed via commercially available software such as Pro Tools or the like and may be performed in addition to or in lieu of live wireless recording of the audio event.

Local audio devices 102 also receive non-audio information (e.g., time reference signals, digital commands, audio, etc.) from other components of recording system 100 via local receiver 302. During synchronous operation of recording system 100, a portion of the received data may be used to synchronize local timecode generator 304 to the master timecode generator integral to one of the components of recording system 100 (e.g., RCU 104, recorder 108, etc.) using a process such as that described below with respect to FIGS. 4A, 4B, and 5 or an equivalent thereof. Alternatively, during asynchronous operation of recording system 100, the received data may include master timecodes from the master timecode generator that may be used to timestamp individual audio samples and/or files such that the audio received at multiple local audio devices 102 may be synchronized post-recording using one of the methods discussed below with respect to FIGS. 9 and 10 or an equivalent thereof.

As described in further detail below with respect to FIG. 5, local audio devices 102 operating in the synchronous mode may require one or more of comparator 334, oscillator 336, and counter 338. In one aspect of the present invention, oscillator 336 is a 48 kilohertz ("kHz") voltage controlled oscillator. However, alternate embodiments of oscillator 336 may be substituted without departing from the scope of the present invention including but not limited to a high speed clock divided to produce 48 kHz. In the embodiment of the present invention depicted in FIG. 3A, oscillator 336 feeds the sample rate input of local ADC 322, as well as counter 338, which provides a time reference for local timecode generator 304. In this configuration, if local ADC 322 is set to operate at 48 kHz, varying the voltage applied to the clock control input of oscillator 336 will proportionately vary the output of oscillator 336 and, consequently, the sample rate of local ADC 322 and the rate at which local timecode generator 304 keeps time.

When local audio devices 102 such as those depicted in FIG. 3A are used in conjunction with recorders 108 that incorporate a single clock to both regulate the speed of the master timecode generator and control the internal recorder ADC sample rate, comparators 334 help maintain synchronization of local audio devices 102 with each other and with recorder 108 by varying the speed of the respective local timecode generators 304 and the sampling rate of the respective local ADCs 322. As per an algorithm or hardwired logic that duplicates the sequence depicted in FIG. 5, or an equivalent thereof, comparators 334 compare the timecodes generated by the master timecode generator with timecodes generated by the locally timecode generator and, if necessary, increase or decrease the speed of the respective local timecode generator 304 and the sampling rate of the respective local ADC 322 such that these speeds are synchronized with the speed of the master timecode generator and the ADC of recorder 108. That is, comparators 334 generate, through software or hardware, the voltage that is applied to the clock control input of the respective oscillator 336 that proportionately varies the sample rate of local ADC 322 and the rate at which local timecode generator 304 keeps time as necessary to maintain synchronization with the sample rate of the ADC of recorder 108 and the master timecode generator, respectively. In this manner, all local audio devices 102 and recorder 108 sample at virtually identical sample rates allowing a wireless recorder 108, or a wireless recorder/receiver combination, to accurately combine multiple independent tracks of audio, wherein each independent track of audio is received from one of the performer's local audio device 102.

Whenever playback of locally recorded audio is required (e.g., to remedy recording errors caused by transmission losses), RCU 104 transmits a digital command to all local audio devices 102 to playback the audio data stored in the respective memories 332 starting with and subsequent to a specific time reference as indicated by a specific timecode. The digital command is received by local receivers 302, which transmit or relay the command to their respective local control unit 310. Thereafter, local control units 310 access the data stored in the respective memory 332 and cause this data to be played or transmitted sequentially via local transmitter 308 starting with the data associated with the requested timecode. The use of timecodes and synchronization of local and master timecode generators, as well as local and recorder audio sampling rates, as discussed herein allows multiple local audio devices 102 to replay audio with the exact timing that occurred during the audio event.

Figure 3B:
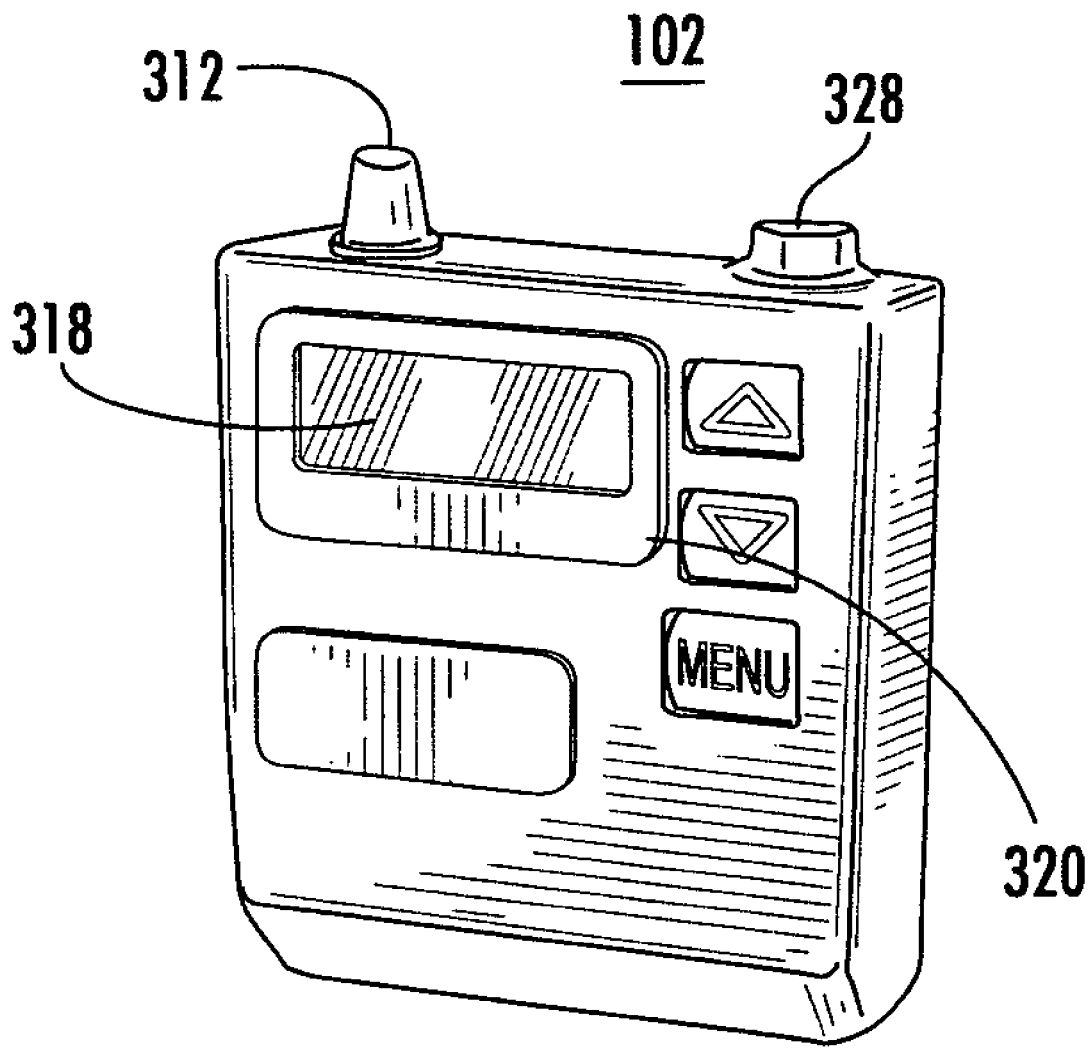
FIG. 3B depicts an external view of a remote control unit in accordance with one embodiment of the present invention.

Local audio devices 102 may be bodypacks such as the local audio device 102 depicted in FIG. 3B. In such an embodiment, display 318 may be a small liquid crystal display ("LCD") or the like and keypad 320 may include a plurality of buttons that allow a user to perform functions including, but not limited to, those that relate to transmitter frequency, receiver frequency, microphone gain, high pass filter, group ID code, unit ID code, transmitter encryption code, and transmitter operating mode. For example, transmitter and receiver frequencies may be adjustable in predetermined frequency steps. Microphone gain may be adjusted, which in turn adjusts the current setting of a preamp such as local preamp 316. Adjustment of the high pass filter may be incorporated to enable and disable, or otherwise adjust, the high pass audio filter of the audio input device such as audio input device 312.

When multiple local audio devices are incorporated in to a group, each local audio device in the group as well as other components of the recording system (e.g., an RCU) may be assigned a group ID. Similarly, the unit ID identifies each specific local audio device within the group of local audio devices.

For local audio devices transmitting encrypted audio and data, the transmitter encryption code is set to match the encryption code of all receiving devices (e.g., an RCU, recorder, or receiver). Correctly setting this code allows the receiving device to properly decrypt the received transmission, while preventing unauthorized users from recording the data.

The operating mode of each local audio device can encompass any one of a number of modes. For example, the operating modes may include USA or European modes, as well as stereo modes. Selection of a specific mode may alter settings such as transmitter bandwidth, audio sampling parameters, and the like.

Although many specific features and functions for the local audio devices have been delineated herein, other features and functions may be added or eliminated without departing from the scope of the present invention.

Additionally, handheld embodiments may include any one of a variety of commercially available batteries to function with the power supply 306 without departing from the scope of the present invention. Power supply 306 may be virtually any power component or combination thereof that is compatible with the other components of local audio device 102 including, but not limited to, a Texas Instruments TPS62000DGS Power Module alone or in combination with a Linear Technology LTC3402 Synchronous Boost Converter.

Alternate embodiments of local audio device 102 are envisioned in which local receiver 302 are eliminated. In one such embodiment, local transmitter 308 is enabled whenever an audio event requiring recording is occurring. Local timecode generator 304 may be designed to generate timecodes whenever local transmitter 308 is enabled. When local transmitter 308 is not operating, the current value of local timecode generator 304 is stored in non-volatile memory to allow local timecode generator 304 to continue counting from the last generated timecode when the local transmitter 308 is re-enabled. Such embodiments include a timecode generator capable of generating unique timecodes for several years without a repeated timecode.

During recording, each local audio device 102 transmits data to one or more receivers and/or recorders. During recording, the receivers and/or recorders automatically detect corrupted audio data received from local audio devices 102 and maintain a list of same. The list of corrupted audio data contains references to the respective local audio device 102 from which the corrupted audio data was received to allow such data to be recovered post-recording.

Post-recording, memories 332 may be removed from each local audio device 102 such that locally recorded data may be retrieved and used to repair the corruption of the audio file generated by the receiver/recorders that occurred due to the receipt of corrupted audio data. Such data recovery may be performed using the multi-memory unit of the present invention or an equivalent. In one embodiment, the multi-memory unit may connect directly to the receivers and/or recorders to allow this equipment to directly retrieve the required audio data. In another embodiment, memories 332 may be connected directly to the receivers/recorders for retrieval of the audio data, thereby eliminating the need for any extraneous equipment such as a personal computer. Identifiers such as local audio device identifiers, track identifiers, performer identifiers, and the like may be decoded from the audio data to allow the file manipulator to more quickly and easily manipulate the audio data.

Since the timecodes generated locally by each local audio device 102 may vary with respect to each other, the receivers, and/or the recorders, the present invention provides a method for ensuring that audio data retrieved from memories 332 is inserted in the proper time sequence with respect to the audio file(s) generated by the receiver/recorders. To achieve this, during recording, the receiver(s) and/or recorders generate or populate a cross-reference table, database, or the like that correlates the timecodes of the audio files generated by the receiver/recorders, as well as the timecodes of all audio data received from all local audio devices 102. That is, the cross-reference mechanism correlates each timecode generated by a receiver or recorder to each timecode generated by each local audio device. In this manner, the timecodes of audio retrieved from memories 332 may be cross-referenced to determine the correlating timecode of the audio file generated by the receiver/recorders. Thereafter, the retrieved audio may optionally be re-stamped with the timecode of the receiver/recorder and inserted in its proper place within the receiver/recorder audio file. In this manner, audio may be wirelessly recorded with zero data loss.

Figure 4A:
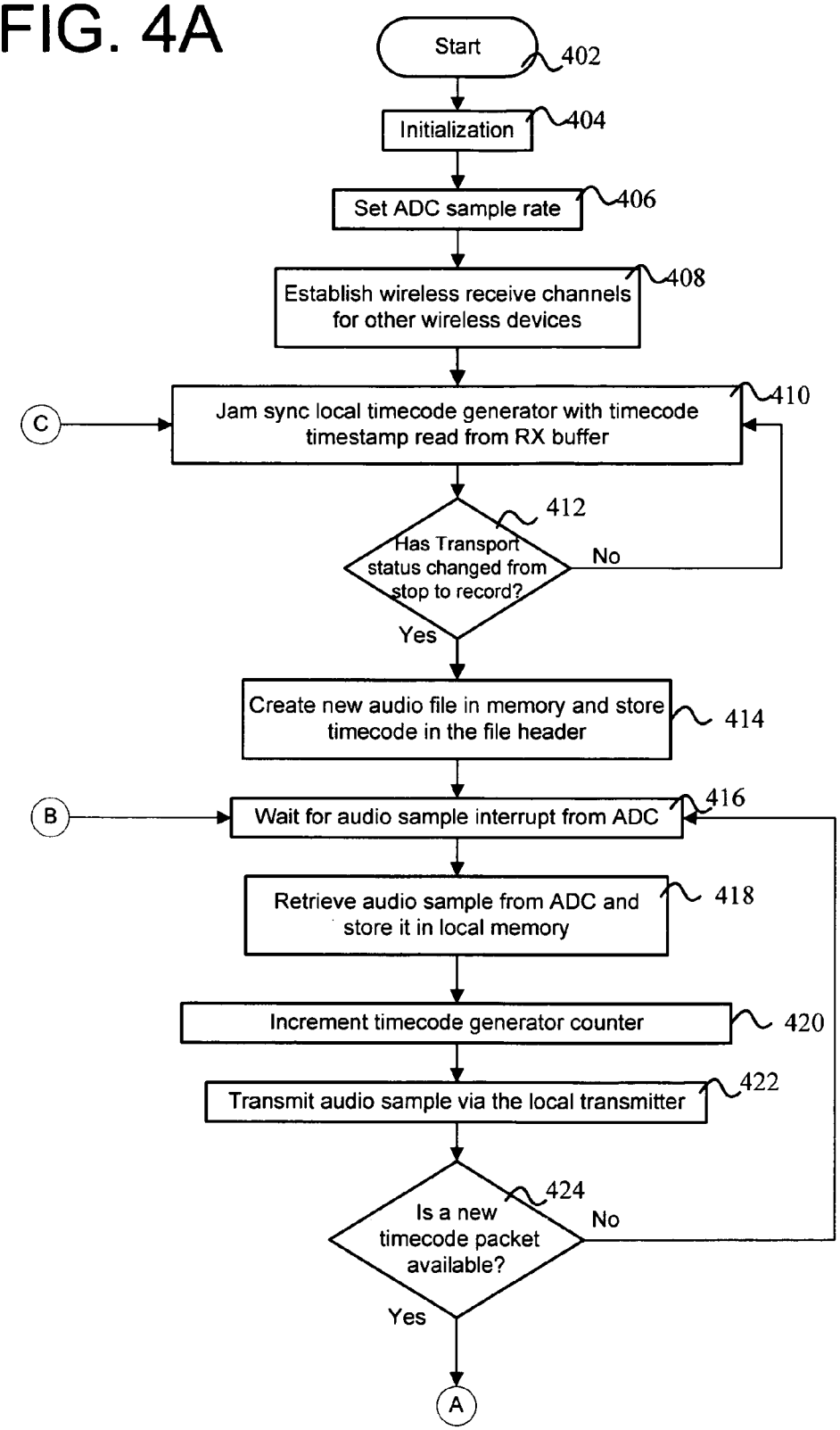
FIGS. 4A and 4B depict a process for operation of a recording system in a synchronous timecode generator mode in accordance with one embodiment of the present invention.

Referring now to FIG. 4A, illustrated is a flow diagram of one embodiment of a process for operation of a recording system such as recording system 100 in synchronous timecode generator mode in accordance with one embodiment of the present invention. Process 400 begins at 402. For example, at 402, one or more performers may each don a local audio device, such as local audio device 102 as described with respect to FIGS. 1, 3A, and 3B. Also, a sound engineer or other personnel may be equipped with a control unit such as RCU 104. Process 402 then proceeds to 404.

At 404, initialization occurs. During initialization, the local control unit such as local control unit 310 or other form of central processing unit is reset. Thereafter, the local transmitter, local receiver, ADC, DAC, and local timecode generator clock are initialized. The process then optionally proceeds to 406, at which the sampling rate of the ADC is set. Alternatively, the sampling rate may be set via hardware or via software executed as part of a separate algorithm. In some embodiments of the present invention, a sample rate of 48 kHz is incorporated.

Next, at 408, wireless receive channels are established between the local audio device and one or more wireless devices such as RCUs (e.g., RCU 104), receivers, and audio recorders. To establish the channel, the local receiver of the audio device receives one or more data packets from the remote wireless device and stores the packets in a designated buffer. For example, when establishing wireless communication with a RCU, the local audio device may receive one or more data packets containing information such as a master timecodes, transport status (i.e., transport mode of an audio recorder), and the like. These packet(s) are then stored in an RX buffer (i.e., a reserved segment of memory used to hold data while it is being processed). Process 400 then proceeds to 410.

At 410, the local control unit reads the master timecode contained in the RX buffer and jam synchronizes the local timecode generator with the master timecode. The jam sync synchronizes the local audio device with the RCU while allowing the local audio device to supply its own timecode. Local supply of synchronized timecodes ensures proper timing during periods in which the master timecodes cannot be read (e.g., the RCU is temporarily unstable, wireless communication dropouts, etc.). Local supply of timecodes also allows local identifiers such as local track identifiers, local audio device identifiers, and the like to be added to the respective local audio device timecode. Such identifiers allow the locally recorded audio to be distinguished from audio recorded by other local audio devices. Such ability to distinguish is particularly useful to quickly and easily identify the audio tracks post-recording.

Next, at 412, process 400 queries the transport status stored in the RX buffer. If at 412, the transport status is stop, process 400 returns to 410. However, if at 412, the transport status is record, process 400 proceeds to 414. At 414, a new audio file is created in memory (e.g., on a flash card) and the newly created file is timestamped. In one aspect Of the present invention, timestamping includes storing the timecode in the file header. Process 400 then proceeds to 416.

At 416, the local control unit waits for an audio sample interrupt from the ADC. Once an audio sample interrupt occurs, process 400 proceeds to 418. At 418, the audio sample is retrieved from the ADC and stored in the local memory. In one aspect of the present invention, the audio sample is stored in the next available address of the local memory. Next, at 420, the timecode generator counter is incremented, thereby indicating that the time period for one sample of audio has elapsed.

Figure 4B:
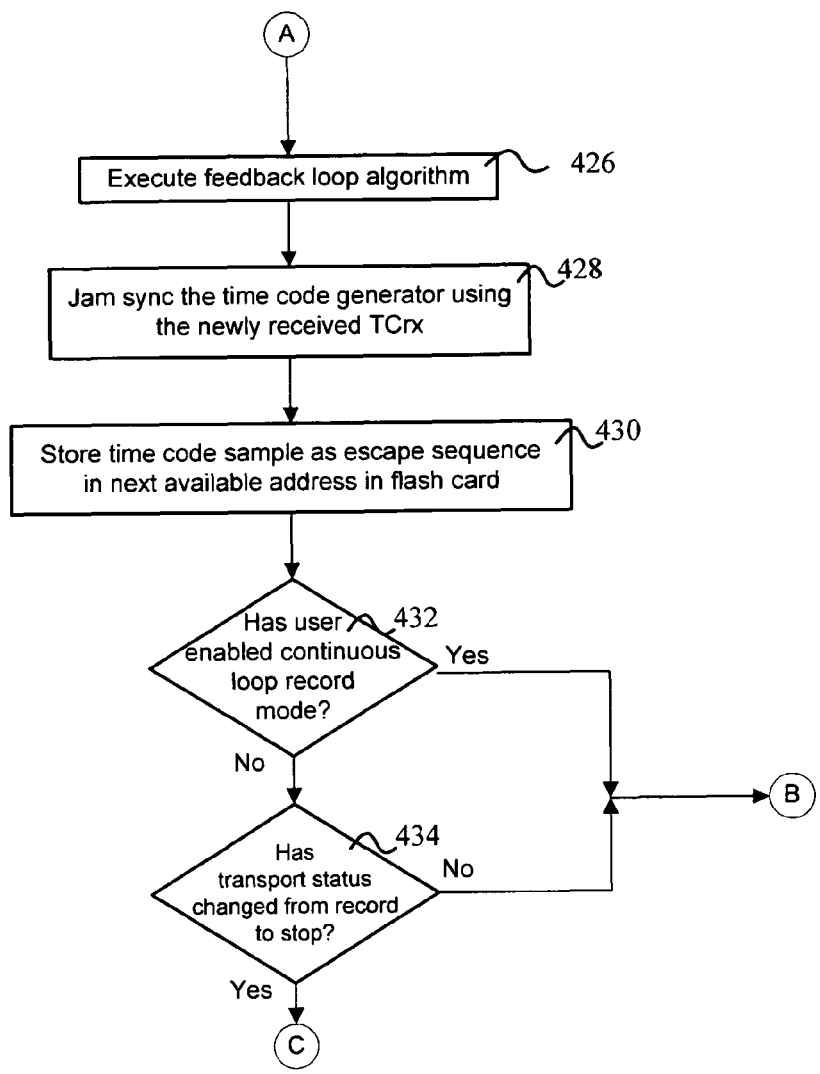

Process 400 then proceeds to 422, at which the local control unit transmits the audio sample through the local transmitter to the other wireless devices such as RCUs, receivers, audio recorders, and the like. For example, audio from multiple local audio devices may be transmitted to a multi-track recorder for recording of the audio event while each local audio device locally records its performer's audio. At 424, process 400 queries the RF buffer of the local receiver to determine the availability of a new master timecode packet. If at 424, a new master timecode packet has not been received from the RF receiver, process 400 returns to 416. However, if at 424, a new master timecode packet has been received, process 400 proceeds to 426 as depicted in FIG. 4B.

At 426, process 400 executes a feedback loop algorithm, which modifies the speed of the local timecode generator as necessary to maintain its synchronization with the master timecode generator (e.g., a timecode generator contained within the RCU or master recorder). This algorithm may be implemented using any one of a variety of methods. In one embodiment of the present invention, a feedback loop algorithm, such as process 500 depicted in FIG. 5, modulates a low-pass filtered feedback error voltage that is supplied by the local control unit directly to the local oscillator. The local oscillator then controls the sample rate of the ADC and the speed of the local timecode generator by supplying the feedback error voltage to the ADC's sample rate input and the local timecode generator's clock control input. Alternatively, a comparator independent of the local control unit may perform the comparison of the master timecodes and the local timecodes and may vary the sample rate of the ADC and the speed of the local timecode generator by directly supplying the feedback error voltage to the oscillator. A variety of hardware and software equivalents of this function may be substituted without departing from the scope of the present invention.

Figure 5:
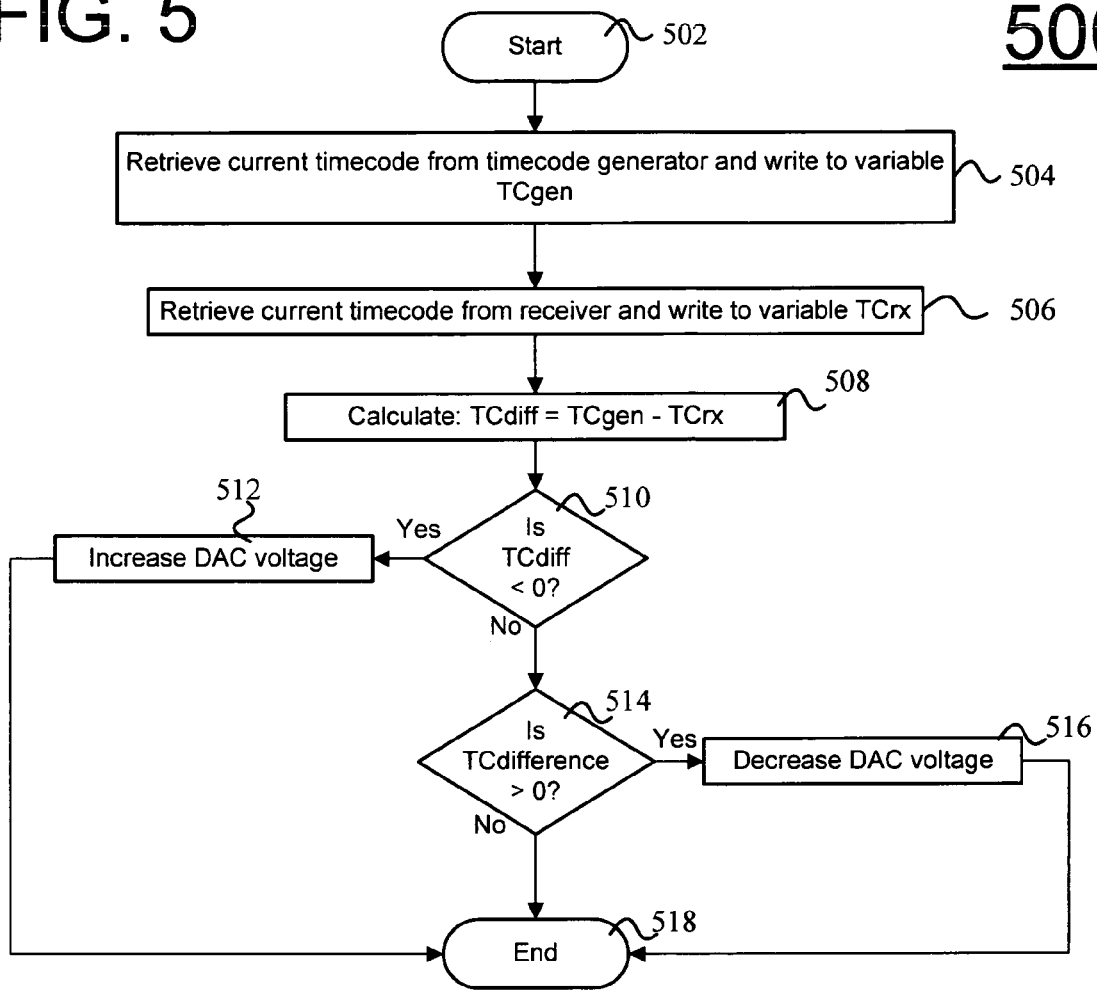
FIG. 5 depicts a process for modifying the speed of a local timecode generator as necessary to maintain its synchronization with a master timecode generator in accordance with one embodiment of the present invention.

Referring now to FIG. 5, the feedback loop algorithm begins at 502. At 504, the current local timecode is retrieved from the timecode generator such as local timecode generator 304 and is written to the variable TCgen. Process 500 proceeds to 506. At 506, the current master timecode is retrieved from the RX buffer of the local receiver and is written to the variable TCrx and process 500 proceeds to 508. At 508, variable TCdiff is calculated by subtracting TCrx from TCgen. Process 500 then proceeds to 510, at which process 500 compares TCdiff to zero. If, at 510, TCdiff is less than zero, process 500 proceeds to 512, at which the feedback error voltage supplied to the local oscillator's DAC by the local control unit is increased above the previously supplied feedback error voltage. The local oscillator's DAC then supplies the new feedback error voltage to the local oscillator, which, in turn, supplies a new clock input voltage to the local timecode generator and a new sample rate input to the ADC. In this manner, the speed of the local timecode generator and the sample rate of the ADC are increased to maintain synchronization with the master timecode generator. However, alternate embodiments of the present invention are envisioned in which only one of either the speed of the local timecode generator or the sample rate of the ADC is modified.

Alternatively, if at 510 TCdiff is not less than zero, process 500 proceeds to 514, at which TCdiff is analyzed to determine if it is greater than zero. If yes, process 500 proceeds to 516 and the feedback error voltage supplied to the local oscillator's DAC by the local control unit is decreased below the previously supplied feedback error voltage. The local oscillator's DAC then supplies the new feedback error voltage to the local oscillator, which, in turn, supplies a new clock input voltage to the local timecode generator and a new sample rate input to the ADC. In this manner, the speed of the local timecode generator and the sample rate of the ADC are decreased to maintain synchronization with the master timecode generator. However, alternate embodiments of the present invention are envisioned in which only one of either the speed of the local timecode generator or the sample rate of the ADC is modified. Furthermore, alternate embodiments are envisioned in which an inverse relationship occurs (e.g., DAC voltage is increased when TCDiff is greater than zero and it is decreased when TCDiff is less than zero).

If TCdiff is neither less than zero as determined at 510 or greater than zero as determined at 514, then TCdiff is equal to zero. In this scenario, the local and master timecode generators are synchronized and, therefore, no adjustment is made to the speed of the local timecode generator. At this point, process 500 ends at 518.

Although FIG. 5 depicts one method of performing a feedback loop, many variations of this feedback loop may be substituted without departing from the scope of the present invention. For example, the feedback loop may be implemented as a digital phased locked loop that re-samples the audio in a manner that simulates a hardwired feedback loop. Also, the feedback loop may include a low pass filter.

Referring back to FIG. 4B, after execution of the feedback loop algorithm at 426, process 400 proceeds to 428. At 428, the local timecode generator is jam synchronized with the newly received master timecode read from the RX buffer. Next, process 400 optionally proceeds to 430, at which a timecode is stored as an escape sequence in the next available address of the local memory. The escape sequence stores a master timecode in addition to the locally generated timestamp. This escape sequence may be used post-processing to resample the audio based upon interpolated master timecode data. Process 400 then proceeds to 432. At 432, process 400 queries the continuous loop record mode. If at 432 the continuous loop record mode is enabled, process 400 returns to 416 to wait for an audio sample interrupt from the ADC as discussed above. However, if at 432, the continuous loop record mode has not been enabled, process 400 proceeds to 434. At 434, process 400 queries the transport status. If at 434 the transport status is record, process 400 returns to 416 to wait for an audio sample interrupt from the ADC as discussed above. However, if at 434, the transport status is stop, process 400 returns to 410, at which process 400 continuously jam synchronizes the local timecode generator with the master timecodes received in the RX buffer until the transport status changes from stop to record at 412.

Figure 6:
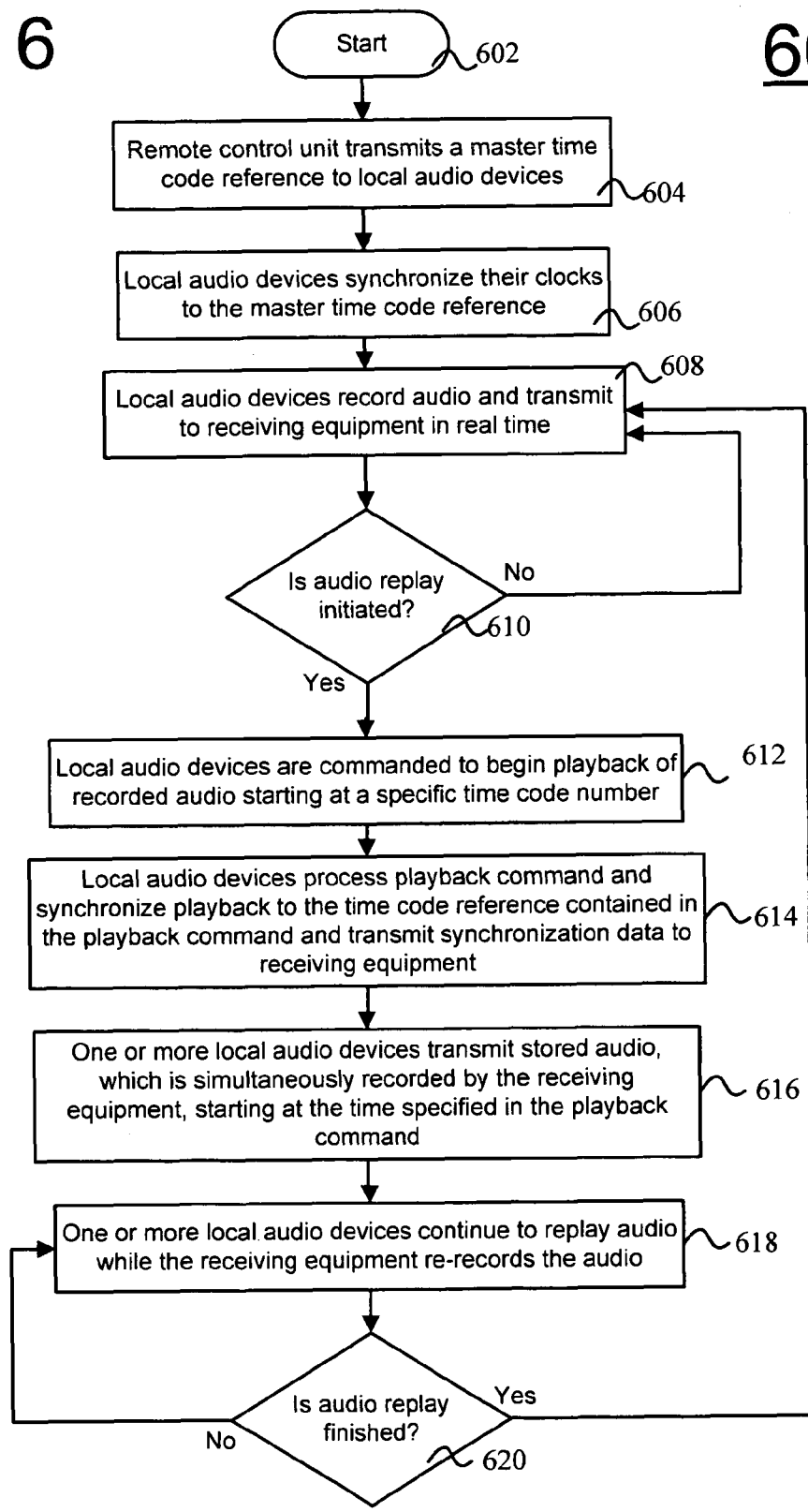
FIG. 6 depicts a process for recording audio and for replaying and re-recording segments of missed audio in accordance with one embodiment of the present invention.

Turning next to FIG. 6, illustrated is a flow diagram of one embodiment of a process for recording audio and for replaying and re-recording segments of missed audio in accordance with embodiments of the present invention. Process 600 begins at 602. For example, at 602, one or more performers may each don a local audio device, such as local audio device 102 as described with respect to FIG. 2A. Process 600 then proceeds to 604.

At 604, a master unit, such as RCU 104, receiver 106, or recorder 108 transmits master timecodes to each local audio device, and process 600 proceeds to 606. At 606, each local audio device synchronizes (e.g., jam syncs) its respective on board local timecode generator with the master timecodes received from the master unit, thereby synchronizing all local audio device timecode generators with the master timecode generator contained within the master unit. Process 600 then proceeds to 608. At 608, local audio devices begin locally recording audio received from an audio input device. This audio is stored in the memory of the respective local audio device with timestamps generated by the local timecode generator. Identifiers such as track identifiers, local audio device identifiers, and the like may also be stored in the memory of the respective local audio device to allow the locally recorded audio to be associated by track, local audio device, or the like post-recording. Each local audio device also simultaneously transmits its received audio to recorders or receiver/recorder combinations such as receivers 106 and recorders 108 in real time. Such audio may be transmitted alone or in combination with its respective timecodes. The audio received from each of the local audio devices (e.g., the local audio device of each performer) may be combined to create one or more multi-track audio files that are stored with master timestamps generated by the receiver/recorder's internal master timecode generator. In some embodiments of the present invention, local timecodes generated by the respective local audio device are stored with the multi-track audio files in addition to the master timestamps.

Process 600 then proceeds to 610. At 610, process 600 queries the initiation of audio replay. The initiation of audio replay may be manual or automatic. For example, if a user detects a loss of audio, the user may manually initiate audio replay beginning at the specific timecode reference at which the transmission error occurred. Alternatively, if a loss of audio is automatically detected by the receiving equipment, a playback request may be sent from the receiving equipment to the controlling unit such as a remote control unit. In response, such controlling unit may command the local audio devices to replay or retransmit the missed audio to the receiving equipment beginning at the timecode at which the loss of data occurred or at a conveniently close time thereto (e.g., zero to ten seconds prior to the loss of data).

If, at 610, audio replay is not initiated either manually or automatically, process 600 returns to 608. However, if, at 610, audio replay is initiated, process 600 proceeds to 612. At 612, a controlling unit, such as RCU 104, sends a signal to the local audio devices requesting playback of the stored audio starting at a specific timecode.

Next, at 614, each local audio device processes the playback command and synchronizes playback to the timecode contained in the playback command. In addition, at least one local audio device transmits the synchronization data to the receiving equipment (e.g., receiver 106, recorder 108, etc.) to synchronize recording of the replayed audio. Process 600 then proceeds to 616. However, in alternate embodiments of the present invention, the receiving equipment and the local audio devices may simultaneously receive the synchronization and time reference data from the transmitting equipment (e.g., the controlling unit).

At 616, one or more local audio devices transmit, or replay, its respective stored audio starting with the audio that corresponds to the time specified by the timecode. The receiving equipment simultaneously records the replayed audio from each of the local audio devices and stores it within the previously recorded audio according to its timecode data. That is, due to the highly accurate synchronization of all of the components of the recording system, the receiving equipment may insert the replayed audio data that was not recorded during the audio event due to wireless transmission errors into the original recording at the nearly the exact time at which the missed audio originally occurred, thereby compensating for any transmission losses. Process 600 then proceeds to 618. At 618, one or more local audio devices continue to replay audio while the receiving equipment records the audio.

At 620, process 600 queries the status of audio replay. If, at 620, the audio has been fully replayed, process 600 proceeds to 608. At 608, the local audio devices may record a new audio event or may replay a different segment of recorded data. Otherwise, if, at 620, all requested audio has not been replayed or re-recorded, process 600 returns to 618.

Figure 7:
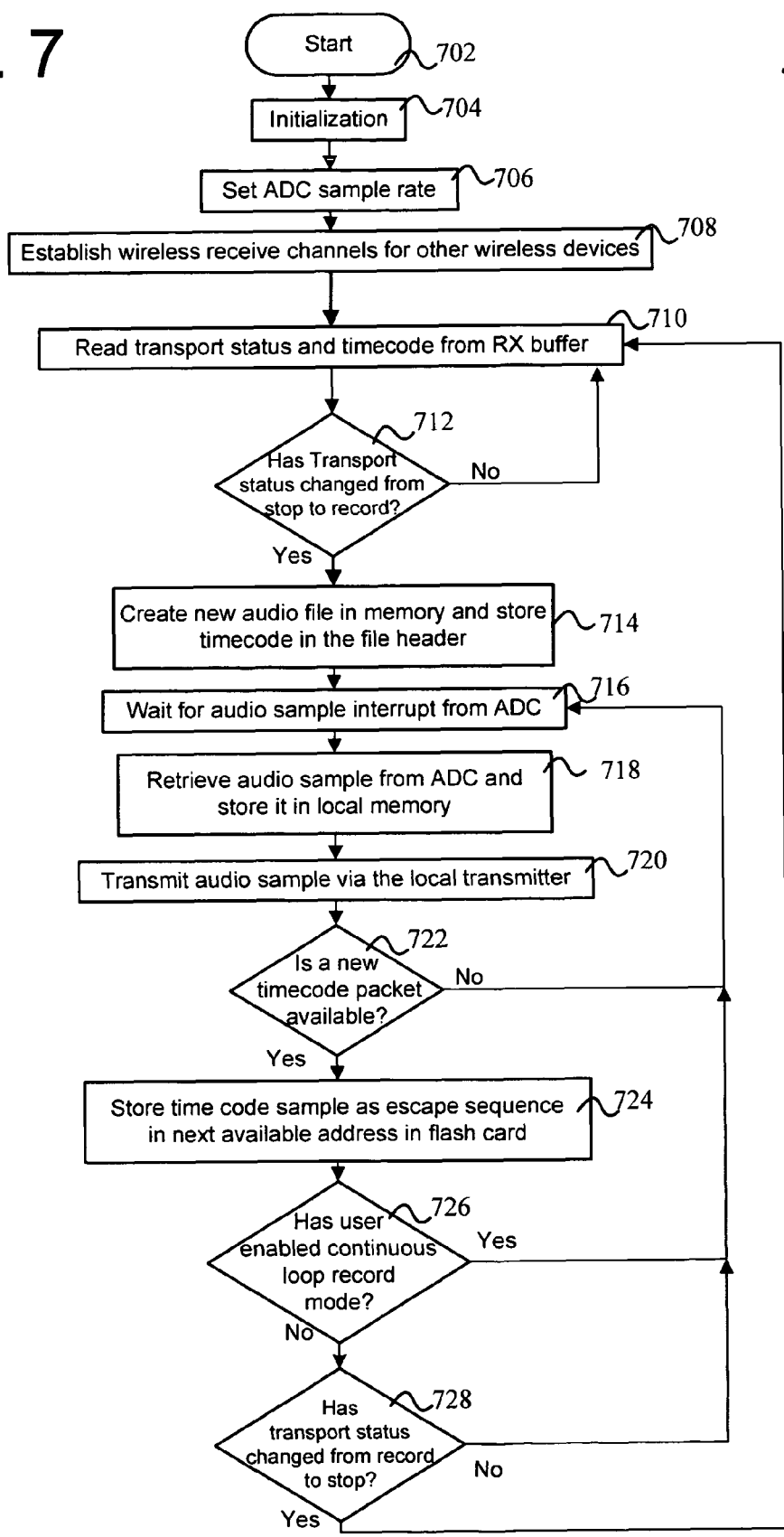
FIG. 7 depicts a process for operation of a recording system in asynchronous timecode generator mode in accordance with one embodiment of the present invention.

Referring now to FIG. 7, illustrated is a flow diagram of one embodiment of a process for operation of a recording system such as recording system 100 in asynchronous timecode generator mode in accordance with one embodiment of the present invention. Process 700 begins at 702. For example, at 702, one or more performers may each don a local audio device, such as local audio device 102 as described with respect to FIGS. 1, 3A, and 3B. Also, a sound engineer or other personnel may be equipped with a control unit such as RCU 104. Process 702 then proceeds to 704.

At 704, initialization occurs. During initialization, the local control unit such as local control unit 310 or other form of central processing unit is reset. Thereafter, the local transmitter, local receiver, ADC, DAC, and clock are initialized. The process then proceeds to 706, at which the sampling rate of the ADC is set. In some embodiments of the present invention, a sample rate of 48 kHz is incorporated.

Next, at 708, wireless receive channels are established between the local audio device and one or more wireless devices such as RCUs (e.g., RCU 104), receivers, and audio recorders. To establish the channel, the local receiver of the audio device receives one or more data packets from the remote wireless device and stores the packets in a designated buffer. For example, when establishing wireless communication with a RCU, the local audio device may receive one or more data packets containing information such as a timecode, transport status (i.e., transport mode of an audio recorder), and the like. These packet(s) are then stored in an RX buffer. Process 700 then proceeds to 710.

At 710, the local control unit reads the transport status and the master timecode contained in the RX buffer. Next, at 712, process 700 queries the transport status. If at 712, the transport status is stop, process 700 returns to 710. However, if at 712, the transport status is record, process 700 proceeds to 714. At 714, a new audio file is created in memory (e.g., on a flash card) and the timecode is stored in the header of the newly created file. Such timecode may optionally include identification information such as track identifiers, local audio device, identifiers, and the like. Or, alternatively, such identification information may be stored in the newly created file in a location other than the timecode. For example, such identification information may be stored in the data stream in the header of the newly created file. However, the present invention is not so limited. Process 700 then proceeds to 716.

At 716, the local control unit waits for an audio sample interrupt from the ADC. Once an audio sample interrupt occurs, process 700 proceeds to 718. At 718, the audio sample is retrieved from the ADC and stored in the local memory. In one aspect of the present invention, the audio sample is stored in the next available address of the local memory. Process 700 then proceeds to 720, at which the local control unit transmits the audio sample through the local transmitter to the other wireless devices such as receivers, audio recorders, and the like.

At 722, process 700 queries the RF buffer of the local receiver to determine the availability of a new master timecode packet. If at 722, a new master timecode packet has not been received from the RF receiver, process 700 returns to 716. However, if at 722, a new master timecode packet has been received, process 700 optionally proceeds to 724. At 724, the timecode is stored as an escape sequence in the next available address of the local memory. Process 700 then proceeds to 726. At 726, process 700 queries the continuous loop record mode. If at 726 the continuous loop record mode is enabled, process 700 returns to 716 to wait for an audio sample interrupt from the ADC as discussed above. However, if at 726, the continuous loop record mode has not been enabled, process 700 proceeds to 728. At 728, process 700 queries the transport status. If at 728 the transport status is record, process 700 returns to 716 to wait for an audio sample interrupt from the ADC as discussed above. However, if at 728, the transport status is stop, process 700 returns to 710, at which process 700 continuously reads the transport status and master timecodes from the RX buffer until the transport status changes from stop to record at 712.

Operation of the present invention in asynchronous mode allows one or more components of local audio devices such as local audio devices 102 (e.g., local timecode generator, comparator, counter, etc.) to be eliminated in embodiments in which the local audio devices utilize master timecodes generated by the master timecode generator rather than locally generated timecodes.

Figure 8:
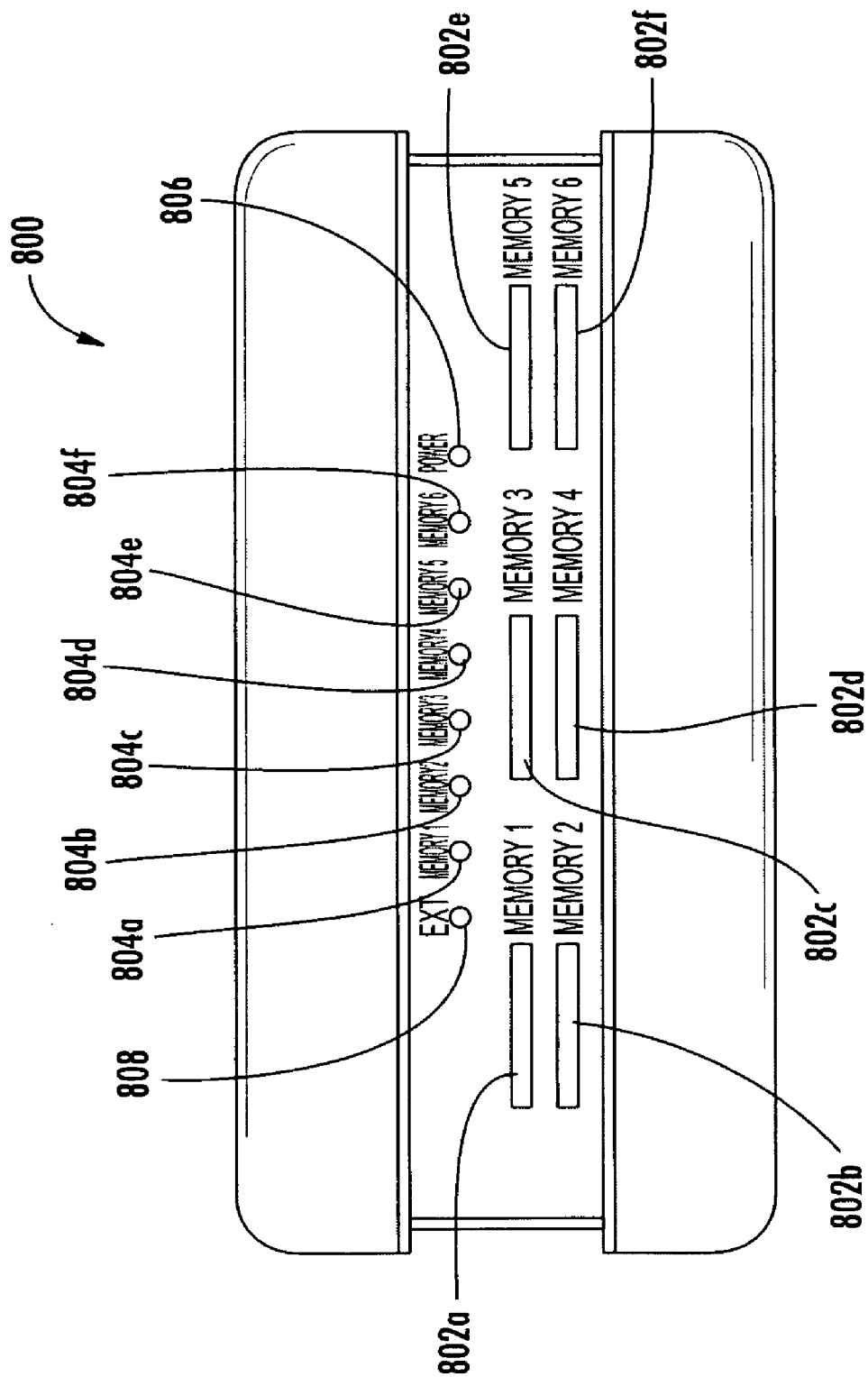
FIG. 8 depicts an external view of a multi-memory unit in accordance with one embodiment of the present invention.

Referring next to FIG. 8, depicted is multi-memory unit 800 for reading and/or reformatting audio files recorded on a plurality of local audio device memories (e.g., memories 332). In its simplest form, such as the embodiment depicted in FIG. 8, multi-memory unit 800 includes a plurality of individual memory ports 802a-802f (e.g., flash memory card drives, compact flash memory card drives, USB thumbdisk ports, etc.). Also optionally included is a plurality of memory status displays 804a-804f to indicate to a user which memory ports 802 are in use. Similarly, power status display 806 and external connection status display 808 may be optionally included to indicate the presence of power and an external connection (e.g., a personal computer), respectively. Multi-memory unit 800 may be equipped with an integral user interface or may be connected to an external interface (e.g., a personal computer) to allow the audio files contained on each memory to be manipulated and/or read.

In one aspect of the present invention, the memory of each local audio device such as local audio device 102 may be removed after completion of a performance, videotaping, etc. Each memory may then be inserted into a corresponding one of memory ports 802. Thereafter, all of the individual audio files may be combined to provide one or more comprehensive audio files. Or, alternatively, each audio file may be individually reformatted or otherwise manipulated prior to creation of one or more comprehensive audio files.

In embodiments of the present invention in which the recording system recorded the audio event in asynchronous mode, or in which long periods (e.g., 8 hours) of recording occurred, multi-memory unit 800 may be used to resample the audio samples to ensure that each audio file's timestamps are properly synchronized. One example of such as process is illustrated in the flowchart of FIG. 9.

In some embodiments of the present invention, multi-memory unit 800 may allow identification information such as track identifiers, local audio device identifiers, and the like to be added to each portion of audio stored in memory 332. In such embodiments, multi-memory unit 800 may have the ability to modify the timecode(s) associated with each portion of audio recorded on each memory 332 to add, modify, or delete the desired identification information. Or, alternatively, multi-memory unit 800 may have the ability to add such identification information to each portion of audio stored in memory 332 in a location other than the timecode (e.g., in a file header).

Referring now to FIG. 9, illustrated is a flow diagram of one embodiment of a process for interpolating timestamps for unstamped audio samples (i.e., audio samples that are not associated with a master timecode timestamp) based upon the timestamps of stamped audio samples (i.e., audio samples that are associated with a master timecode timestamp), and resampling the audio samples to include the interpolated timestamps in accordance with embodiments of the present invention. After recording of an audio event, the audio data stored in the memory of the local audio device (e.g., memory 332) will typically be stored as an audio sample stream wherein approximately one out of every one thousand to one hundred thousand samples includes a timestamp generated by a remote master timecode generator. However, the interval between timestamped audio samples may be greater than the aforementioned interval if the wireless timecode link was less reliable than a standard wireless link.

The resampling process depicted in FIG. 9, and equivalents thereof, analyze the occurrence of the relatively sparse timestamped audio samples to generate a linear interpolation or a best fit curve. This curve is then used to interpolate timestamps for the unstamped audio samples. After the timestamp of each audio sample has been interpolated, the audio samples may then be re-sampled such that the audio samples are now synchronized with samples generated by the master timecode generator. In one aspect of the present invention, the audio samples are resampled based upon the calculated curve to simulate the condition of an ADC whose sample rate input was driven directly by the master timecode generator's source.

If all of the audio from all local audio devices is resampled in this manner, each resulting resampled audio file appears as if it was originally sampled with an accurate audio sample clock derived from the master timecode source. This resampling allows each audio file to include a single timestamp that marks the master timecode of the first audio sample of the audio file. Furthermore, since the audio files now appear as if they have been sampled by an extremely accurate audio sample clock, each audio sample's timestamp may be accurately calculated based solely on the audio sample rate and the timestamp of the first audio sample of the audio file. This condition allows the audio files to be formatted and/or stored as a standard timecoded broadcast .WAV file, thereby allowing them to be read, edited, etc. using standard, commercially-available editing systems. That is, the files may be processed in the same manner as if the audio file had been generated by a standard multi-track audio recorder. Such condition allows the present invention to be easily integrated with other industry standard recording equipment.

One such resampling process is illustrated in FIG. 9. Process 900 begins at 902. For example, at 902, one or more local audio device memories may be removed from its respective local audio device and may be inserted into a multi-memory unit 800, or an equivalent thereof. Process 902 then proceeds to 904.

At 904, process 900 determines the desired starting and ending timecodes and stores this data in the variables TimeCodeStart and TimeCodeEnd, respectively. The desired starting and ending timecodes may be input by a user or may be suggested or automatically determined by the algorithm. Process 900 then proceeds to 906. At 906, a variable, i, is initialized to a value of zero. The variable i corresponds to the position of audio samples or data points in a data array represented by the variable AudioSample[i]. Process 900 then proceeds to 908.

At 908, process 900 begins an iterative search for the audio file that matches the desired starting timecode of the output file by comparing the value of TimeCodeStart with the value of the timecode of AudioSample[i]. If, at 908, the value of TimeCodeStart is equal to the value of the AudioSample[i] timecode, process 900 proceeds to 912. However, if at 908 the value of TimeCodeStart is not equal to the value of the AudioSample[i] timecode, process 900 proceeds to 910. At 910, the variable i is increased by a value of one thereby allowing the value located in the next position of the audio sample array to be compared to the value of TimeCodeStart when process 900 returns to 908.

If the value of TimeCodeStart is equal to the value of the AudioSample[i] timecode, process 900 proceeds to 912. At 912, a variable, n, is initialized to a value of one. The variable n is added to the variable i to allow process 900 to continue to traverse the audio sample array while maintaining the location of the audio sample at the starting timecode, which is represented by the variable AudioSample[i]. Process 900 then proceeds to 914. At 914, the value of the AudioSample[i+n] timecode is compared to the value of TimeCodeEnd: If at 914, the value of the AudioSample[i+n] timecode is greater than or equal to the value of TimeCodeEnd, process 900 proceeds to 916. At 916, the value of the AudioSample[i+n] timecode is again compared to the value of TimeCodeEnd. If at 914, the value of the AudioSample[i+n] timecode is greater than the value of TimeCodeEnd, process 900 proceeds to 928, at which process 900 terminates. However, if at 916, the value of the AudioSample[i+n] timecode is equal to the value of TimeCodeEnd, process 900 proceeds to 922.

Conversely, if at 914, the value of the AudioSample[i+n] timecode is less than the value of TimeCodeEnd, process 900 proceeds to 918. At 918, the value of the AudioSample[i+n] timecode is compared to the value of CurrentTimeCodeEscapeSequence. If, at 918, the value of the AudioSample[i+n] timecode is not equal to the value of TimeCodeEscapeSequence, process 900 proceeds to 920 where the variable n is increased by one and process 900 returns to 914. However, if at 918, the value of the AudioSample[i+n] timecode is equal to the value of TimeCodeEscapeSequence, process 900 proceeds to 922.

At 922, the average time period "T" that elapsed between the audio samples that occurred between AudioSample[i] and AudioSample[i+n] may be calculated by subtracting the value of the timecode of AudioSample[i] from the value of the timecode of AudioSample[i+n] and dividing by n, wherein n is now equivalent to the number of audio samples that occurred between the current timestamped audio sample and the previous timestamped audio sample. Process 900 then proceeds to 924. At 924, AudioSamples[i] through AudioSamples[i+n] are re-sampled at any desired sample rate based upon the value of T as calculated in 922, or any other desired sample rate, using an audio resampling algorithm (e.g., linear interpolation). Process 900 then proceeds to 926, at which the variable i is set to a value equal to the current value of i plus the current value of n and process 900 returns to 912. The iterative process continues until the value of the AudioSample[i+n] timecode is greater than the value of TimeCodeEnd, whereby process 900 proceeds to 928, at which process 900 terminates.

A similar interpolation algorithm, such as the algorithm depicted in FIG. 10, may be incorporated to break down single large audio files (e.g., an audio file recording the filming of multiple movie takes over a continuous eight hour period as a single eight-hour audio file) into smaller, more useful files (e.g., one audio file per take). These smaller files will allow the audio recorded locally by the local audio devices to be more easily matched or synchronized with the individual audio files recorded by a master recorder such as recorder 108.

In one use of an embodiment of the present invention, multiple local audio devices store audio samples with wirelessly-received timecode and transport status samples continuously for the entire duration of the work day (e.g., an 8 hour period). In a typical scenario, while the local audio devices are recording continuously, a technician intermittently records segments of the eight-hour audio event. For example, in a film setting, each segment would typically represent a movie 'take' and might range from one to five minutes in duration. Consequently, the master recorder generates individual audio files (i.e., at least one audio file for each recorded segment such as a movie take), whereas each local audio device generates one massive audio file. Therefore, there is a need for a method of segmenting each large local audio file into smaller audio files that correspond to the segments recorded by the master recorder.

The segmentation method (i.e., the method of segmenting the large local audio devices' files to match the multiple, smaller master recorder's audio file) requires knowledge of which portions of the single local audio device audio file are important and which portions can be discarded. This information can be inferred from the transport status of the master recorder since it is typically operated by someone with this knowledge. Therefore, when the transport status of the master recorder changes from stop to record, it can be inferred that a new master recorder audio file begins, and, subsequently, when the transport status of the master recorder changes from record to stop, it can be inferred that the same master recorder audio file has ended. In addition, when the transport status of the master recorder remains in the stop mode, it can be inferred that the audio recorded by the local audio device during this time period may be discarded. This audio may be discarded post-processing as per algorithms such as that depicted in FIG. 10 or during live recording.

In embodiments of the present invention in which such data is discarded during live recording, the transport status and master timecode of the master recorder are wirelessly transmitted to the local audio devices. This information may be processed by the local audio devices to allow them to create a new audio file with the current master timecode of the master recorder whenever the received transport status and master timecode indicate that the transport status has changed from stop to record. Similarly, the local audio devices may end the newly created audio file when the received transport status indicates that it has changed from record to stop. In this scenario, the resulting local audio device files will automatically be segmented and will each be marked with a master timestamp at the beginning of each file.

However, in embodiments of the present invention in which unimportant audio is not discarded during live recording and, therefore, one or more large audio files are created, the large audio files may be segmented as per a process such as process 1000 as illustrated in FIG. 10. Process 1000 begins at 1002 at which one or more local audio devices have continuously recorded a lengthy quantity of audio data. Process 1000 then proceeds to 1004.

At 1004, a copy of the audio file directory containing the segmented audio files that correspond to the same time period as the local audio device's single large audio file is obtained from the master recorder. Process 1000 then proceeds to 1006. At 1006, a variable y is initialized to a value of zero. The variable y corresponds to the number of each file contained in the audio file directory copied from the master recorder. Process 1000 then proceeds to 1008, at which the variable y is increased by one and a variable x is initialized to a value of one. The variable x corresponds to the position of each audio sample within a particular file. Process 1000 then proceeds to 1010, at which the copied audio file directory is queried to determine if a file[y] (i.e., the file named with the number that corresponds to the value of y) exists in the audio file directory. If no, process 1000 proceeds to 1028 and terminates.

If file[y] does exist, process 1000 proceeds to 1012, at which process 1000 determines the starting and ending timecodes for file[y] and stores them in the variables TimeCodeStart and TimeCodeEnd, respectively. Process 1000 then proceeds to 1014, at which process 1000 compares the value of TimeCodeStart to the value of the timecode associated with AudioSample[x] stored in the memory of the local audio device. If at 1014 the value of TimeCodeStart is not equal to the value of the timecode associated with AudioSample[x], process 1000 proceeds to 1016. At 1016, the variable x is increased by one and process 1000 returns to 1014. In this manner, TimeCodeStart is compared to each consecutive AudioSample[x] until the AudioSample timestamped with a value equal to TimeCodeStart is found. In some embodiments of the present invention, process 1000, or an equivalent thereof, is performed after process 900, or an equivalent thereof, to ensure that each of the audio samples has a timestamp (e.g., an interpolated timestamp).

When the AudioSample[x] having a timecode equivalent to TimeCodeStart is found at 1014, process 1000 proceeds to 1018. At 1018, AudioSample[x] is extracted and process 1000 proceeds to 1020, at which the variable x is increased by one and process 1000 proceeds to 1022. At 1022, process 1000 compares the value of TimeCodeEnd to the value of the timecode associated with AudioSample[x]. If at 1022, the value of TimeCodeEnd is not equal to the value of the AudioSample[x] timecode, process 1000 returns to 1018, whereupon audio samples are consecutively extracted until the timecode of the current AudioSample[x] equals TimeCodeEnd. If, at 1022, the value of TimeCodeEnd is equal to the value of the timecode of AudioSample[x], process 1000 proceeds to 1024, at which the final AudioSample[x] of the segmented audio file is extracted and the audio file is saved at 1026.

Process 1000 then proceeds to 1008, at which the variable y is increased by one and process 1000 proceeds to 1010 at which the audio file directory is queried to determine the existence of file [y]. If file[y] exists, process 1000 proceeds to 1012 and it continues thereafter as described above. However, if at 1010, it is determined that file[y] does not exist, process 1000 proceeds to 1028, at which it terminates.

Although several processes have been disclosed herein as software, it is appreciated by one of skill in the art that the same processes, functions, etc. may be performed via hardware or a combination of hardware and software. Similarly, although the present invention has been disclosed with respect to wireless systems, these concepts may be applied to hardwired systems and hybrid hardwired and wireless systems without departing from the scope of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A system for recording locally generated audio comprising:
    at least one master timecode generator for generating a plurality of master timecodes; and
    at least one local audio device wearable by a creator of said locally generated audio including:
        at least one local audio device receiver for receiving at least one of the group consisting of digital commands, said master timecodes, and non-local audio data;
        at least one audio input port for receiving locally generated audio from an audio input device;
        at least one memory; and
        at least one control unit electrically coupled to said local audio device receiver, said audio input device, and said memory for creating local audio data from said locally generated audio and storing said local audio data in said memory;
    wherein said local audio data includes stamped local audio data and unstamped local audio data;
    wherein said stamped local audio data includes at least one first timestamp to reference at least a portion of said local audio data to at least one of said master timecodes; and
    wherein said unstamped local audio data does not include a reference to said master timecodes.

2. A system according to claim 1, wherein said local audio data includes at least one identifier selected from the group consisting of track identifiers, local audio device identifiers, performer identifiers, and combinations thereof.

3. A system according to claim 1, said system further comprising:
    at least one remote control unit having an RCU transmitter capable of wirelessly transmitting digital commands;
    wherein said remote control unit controls at least one function of said local audio devices via transmission of at least one of said digital commands; and
    wherein said function includes at least one of the group consisting of adding said track identifier to at least a portion of said local audio data, deleting said track identifier from at least a portion of said local audio data, altering said track identifier associated with at least a portion of said local audio data, adding said local audio device identifier to at least a portion of said local audio data, deleting said local audio device identifier from at least a portion of said local audio data, altering said local audio device identifier associated with at least a portion of said local audio data, adding said performer identifier to at least a portion of said local audio data, deleting said performer identifier from at least a portion of said local audio data, altering said performer identifier associated with at least a portion of said local audio data and combinations thereof.

4. A system according to claim 1, said system further comprising:
    a multi-memory unit including:
        at least one memory unit interface for connection to at least a portion of said memory; and
        a user interface for manipulating said local audio data contained in said at least a portion of said memory;
    wherein said manipulation includes at least one of the group consisting of adding said track identifier to at least a portion of said local audio data, deleting said track identifier from at least a portion of said local audio data, altering said track identifier associated with at least a portion of said local audio data, adding said local audio device identifier to at least a portion of said local audio data, deleting said local audio device identifier from at least a portion of said local audio data, altering said local audio device identifier associated with at least a portion of said local audio data, adding said performer identifier to at least a portion of said local audio data, deleting said performer identifier from at least a portion of said local audio data, altering said performer identifier associated with at least a portion of said local audio data, and combinations thereof.

5. A system according to claim 4, wherein said manipulation is performed via commercially available software.

6. A system according to claim 1, wherein said master timecode includes at least one of the group consisting of time data, frame data, timecode type, recorder transport status, name of scene, name of take, track identifier, and combinations thereof.

7. A system for recording locally generated audio comprising:
    at least one master timecode generator for generating a plurality of master timecodes; and
    at least one local audio device wearable by a creator of said locally generated audio including:
        at least one local audio device receiver for receiving at least one of the group consisting of digital commands and said master timecodes;
        at least one audio input port for receiving locally generated audio from an audio input device;
        at least one memory;
        at least one local timecode generator for generating a plurality of local timecodes; and
        at least one control unit electrically coupled to said local audio device receiver, said audio input device, said memory, and said local timecode generator for creating stamped local audio data and storing said stamped local audio data in said memory;

wherein said stamped local audio data includes at least one local timestamp to reference at least a portion of said stamped local audio data to at least one of said local timecodes; and wherein said stamped local audio data includes at least one identifier selected from the group consisting of track identifiers, local audio device identifiers, performer identifiers, and combinations thereof.

8. A system according to claim 7, said system further comprising:

at least one remote control unit having an RCU transmitter capable of wirelessly transmitting digital commands;

wherein said remote control unit controls at least one function of said local audio devices via transmission of at least one of said digital commands; and wherein said function includes at least one of the group consisting of adding said track identifier to at least a portion of said stamped local audio data, deleting said track identifier from at least a portion of said stamped local audio data, altering said track identifier associated with at least a portion of said stamped local audio data, adding said local audio device identifier to at least a portion of said stamped local audio data, deleting said local audio device identifier from at least a portion of said stamped local audio data, altering said local audio device identifier associated with at least a portion of said stamped local audio data, adding said performer identifier to at least a portion of said stamped local audio data, deleting said performer identifier from at least a portion of said stamped local audio data, altering said performer identifier associated with at least a portion of said stamped local audio data, and combinations thereof.

9. A system according to claim 7, said system further comprising:

a multi-memory unit including:
at least one memory unit interface for connection to at least a portion of said memory; and
a user interface for manipulating said local audio data contained in said at least a portion of said memory;
wherein said manipulation includes at least one of the group consisting of adding said track identifier to at least a portion of said local audio data, deleting said track identifier from at least a portion of said local audio data, altering said track identifier associated with at least a portion of said local audio data, adding said local audio device identifier to at least a portion of said local audio data, deleting said local audio device identifier from at least a portion of said local audio data, altering said local audio device identifier associated with at least a portion of said local audio data, adding said performer identifier to at least a portion of said local audio data, deleting said performer identifier from at least a portion of said local audio data, altering said performer identifier associated with at least a portion of said local audio data, and combinations thereof.

10. A system according to claim 9, wherein said manipulation is performed via commercially available software.

11. A system according to claim 7, wherein said master timecode includes at least one of the group consisting of time data, frame data, timecode type, recorder transport status, name of scene, name of take, track identifier, and combinations thereof.

12. A method of wirelessly recording local audio, said method comprising:

locally receiving said local audio generated by at least one performer during an audio event;

wirelessly transmitting said local audio to at least one of the group consisting of a recorder, a receiver, and combinations thereof;

locally recording said local audio as local audio data in at least one memory of at least one local audio device; and remotely recording said transmitted local audio via at least one of the group consisting of a recorder, a receiver, and combinations thereof as remote audio data;

wherein at least a portion of said local audio data is retrieved during or subsequent to said audio event and is combined with said remote audio data;

wherein said local audio data includes at least one identifier selected from the group consisting of track identifiers, local audio device identifiers, performer identifiers, and combinations thereof.

13. A method according to claim 12, said method further comprising the step of:

locally receiving or generating a plurality of master timecodes;

wherein said local audio data includes stamped local audio data and unstamped local audio data;

wherein said stamped local audio data includes at least one first timestamp to reference at least a portion of said local audio data to at least one of said master timecodes;

wherein said unstamped local audio data does not include a reference to said master timecodes;

wherein said master timecode includes at least one of the group consisting of time data, frame data, timecode type, recorder transport status, name of scene, name of take, track identifier, and combinations thereof.

14. A method according to claim 12, said method further comprising:

remotely controlling at least one function of at least one of said local audio device via at least one remote control unit;

wherein said function includes at least one of the group consisting of adding said track identifier to at least a portion of said local audio data, deleting said track identifier from at least a portion of said local audio data, altering said track identifier associated with at least a portion of said local audio data, adding said local audio device identifier to at least a portion of said local audio data, deleting said local audio device identifier from at least a portion of said local audio data, altering said local audio device identifier associated with at least a portion of said local audio data, adding said performer identifier to at least a portion of said local audio data, deleting said performer identifier from at least a portion of said local audio data, altering said performer identifier associated with at least a portion of said local audio data, and combinations thereof.

15. A method according to claim 12, further comprising:

manipulating said local audio data contained in at least a portion of said memory;

wherein said manipulation includes at least one of the group consisting of adding said track identifier to at least a portion of said memory, deleting said track identifier from at least a portion of said memory, altering said track identifier associated with at least a portion of said memory, adding said local audio device identifier to at least a portion of said memory, deleting said local audio device identifier from at least a portion of said memory, altering said local audio device identifier associated with at least a portion of said memory, adding said performer identifier to at least a portion of said local audio data, deleting said performer identifier from at least a portion of said local audio data, altering said performer identifier associated with at least a portion of said local audio data, and combinations thereof.

16. A method according to claim 15, wherein said manipulation is performed via commercially available software.

17. A method of recording local audio, said method comprising the steps of:
locally receiving said local audio generated by at least two performers during an audio event;
locally recording said local audio as local audio data in at least one memory of at least one local audio device; and
locally receiving or generating a plurality of master timecodes;
wherein said local audio data for each of said performers is retrieved from said local audio devices subsequent to said audio event and is combined to create a single multi-track audio file;
wherein said local audio data includes at least one identifier selected from the group consisting of track identifiers, local audio device identifiers, performer identifiers, and combinations thereof;
wherein said local audio data includes stamped local audio data and unstamped local audio data;
wherein said stamped local audio data includes at least one first timestamp to reference at least a portion of said local audio data to at least one of said master timecodes;
wherein said unstamped local audio data does not include a reference to said master timecodes; and
wherein said master timecode includes at least one of the group consisting of time data, frame data, timecode type, recorder transport status, name of scene, name of take, track identifier, and combinations thereof.

18. A method according to claim 17, further comprising:
remotely controlling at least one function of at least one of said local audio device via at least one remote control unit;
wherein said function includes at least one of the group consisting of adding said track identifier to at least a portion of said local audio data, deleting said track identifier from at least a portion of said local audio data, altering said track identifier associated with at least a portion of said local audio data, adding said local audio device identifier to at least a portion of said local audio data, deleting said local audio device identifier from at least a portion of said local audio data, altering said local audio device identifier associated with at least a portion of said local audio data, adding said performer identifier to at least a portion of said local audio data, deleting said performer identifier from at least a portion of said local audio data, altering said performer identifier associated with at least a portion of said local audio data, and combinations thereof.

19. A method according to claim 17, further comprising:
manipulating said local audio data contained in at least a portion of said memory;
wherein said manipulation includes at least one of the group consisting of adding said track identifier to at least a portion of said memory, deleting said track identifier from at least a portion of said memory, altering said track identifier associated with at least a portion of said memory, adding said local audio device identifier to at least a portion of said memory, deleting said local audio device identifier from at least a portion of said memory, altering said local audio device identifier associated with at least a portion of said memory, adding said performer identifier to at least a portion of said local audio data, deleting said performer identifier from at least a portion of said local audio data, altering said performer identifier associated with at least a portion of said local audio data, and combinations thereof.

20. A method according to claim 19, wherein said manipulation is performed via commercially available software.

* * * * *